(12) United States Patent
Fritzinger

(10) Patent No.: US 11,589,878 B2
(45) Date of Patent: Feb. 28, 2023

(54) CUSTOMIZED PATIENT-SPECIFIC SURGICAL INSTRUMENT SYSTEMS AND METHODS

(71) Applicant: DePuy Synthes Products, Inc., Raynham, MA (US)

(72) Inventor: Daniel D. Fritzinger, Warsaw, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 388 days.

(21) Appl. No.: 16/860,865

(22) Filed: Apr. 28, 2020

(65) Prior Publication Data

US 2020/0253618 A1 Aug. 13, 2020

Related U.S. Application Data

(63) Continuation of application No. 15/878,710, filed on Jan. 24, 2018, now Pat. No. 10,631,878.

(51) Int. Cl.

| A61B 17/15 | (2006.01) |
|---|---|
| A61B 34/10 | (2016.01) |
| A61B 17/17 | (2006.01) |
| A61B 17/00 | (2006.01) |
| A61B 17/56 | (2006.01) |

(52) U.S. Cl.
CPC .......... *A61B 17/155* (2013.01); *A61B 17/157* (2013.01); *A61B 17/1764* (2013.01); *A61B 34/10* (2016.02); *A61B 17/154* (2013.01); *A61B 2017/00526* (2013.01); *A61B 2017/568* (2013.01); *A61B 2034/108* (2016.02)

(58) Field of Classification Search
CPC .... A61B 17/155; A61B 17/157; A61B 17/154
See application file for complete search history.

(56) References Cited

U.S. PATENT DOCUMENTS

| 4,487,203 A | 12/1984 | Androphy |
|---|---|---|
| 4,703,751 A * | 11/1987 | Pohl ..................... A61B 17/155 606/53 |
| 7,468,075 B2 | 12/2008 | Lang et al. |

(Continued)

FOREIGN PATENT DOCUMENTS

| AU | 2017200804 A1 | 2/2017 |
|---|---|---|
| CA | 2447694 A1 | 12/2002 |

(Continued)

OTHER PUBLICATIONS

International Search Report, International Application No. PCT/IB2019/050234, dated May 10, 2019, 7 pages.

*Primary Examiner* — Christian A Sevilla
(74) *Attorney, Agent, or Firm* — Barnes & Thornburg LLP

(57) ABSTRACT

An orthopaedic surgical instrument comprising a metallic customized patient-specific surgical instrument is disclosed. The metallic customized patient-specific surgical instrument includes a base plate sized to be positioned on a resected surface of a distal end of a patient's femur, an anterior resection guide body attached to, and extending from, the distal surface of the base plate to a free distal end, a posterior resection guide body attached to, and extending from, the distal surface to a free distal end, and a pair of chamfer resection guide bodies attached to, and extending from, the distal surface.

20 Claims, 25 Drawing Sheets

(56) References Cited

U.S. PATENT DOCUMENTS

| | | |
|---|---|---|
| 7,534,263 B2 | 5/2009 | Burdulis, Jr. et al. |
| 7,615,054 B1 | 11/2009 | Bonutti |
| 7,747,305 B2 | 6/2010 | Dean et al. |
| 7,983,777 B2 | 7/2011 | Melton et al. |
| 8,083,745 B2 | 12/2011 | Lang et al. |
| 8,167,888 B2 | 5/2012 | Steffensmeier |
| 8,234,097 B2 | 7/2012 | Steines et al. |
| 8,257,360 B2 | 9/2012 | Richard et al. |
| 8,377,066 B2 | 2/2013 | Katrana et al. |
| 8,439,926 B2 | 5/2013 | Bojarski et al. |
| 8,500,740 B2 | 8/2013 | Bojarski et al. |
| 8,617,175 B2 | 12/2013 | Park et al. |
| 8,623,026 B2 | 1/2014 | Wong et al. |
| 8,916,248 B2 | 12/2014 | McCrea et al. |
| 9,675,471 B2 | 6/2017 | Bojarski et al. |
| 10,251,654 B2 | 4/2019 | Fritzinger |
| 10,537,343 B2 | 1/2020 | Fritzinger |
| 2002/0068979 A1 | 6/2002 | Brown et al. |
| 2003/0045883 A1 | 3/2003 | Chow et al. |
| 2003/0100907 A1 | 5/2003 | Rosa et al. |
| 2006/0122617 A1 | 6/2006 | Lavallee et al. |
| 2009/0024131 A1 | 1/2009 | Metzger et al. |
| 2009/0087276 A1* | 4/2009 | Rose ............... A61B 17/155 409/79 |
| 2009/0088753 A1 | 4/2009 | Aram et al. |
| 2009/0131941 A1 | 5/2009 | Park et al. |
| 2009/0222014 A1 | 9/2009 | Bojarski et al. |
| 2010/0023015 A1 | 1/2010 | Park |
| 2010/0185202 A1 | 7/2010 | Lester et al. |
| 2010/0212138 A1 | 8/2010 | Carroll et al. |
| 2010/0217270 A1 | 8/2010 | Polinski et al. |
| 2011/0087332 A1 | 4/2011 | Bojarski et al. |
| 2012/0041446 A1 | 2/2012 | Wong et al. |
| 2012/0109135 A1 | 5/2012 | Bailey |
| 2012/0123422 A1 | 5/2012 | Agnihotri et al. |
| 2012/0209394 A1 | 8/2012 | Bojarski et al. |
| 2012/0277751 A1 | 11/2012 | Catanzarite et al. |
| 2012/0303131 A1 | 11/2012 | Chana |
| 2012/0323246 A1 | 12/2012 | Catanzarite et al. |
| 2013/0296874 A1 | 11/2013 | Chao |
| 2013/0317510 A1 | 11/2013 | Couture et al. |
| 2014/0094814 A1 | 4/2014 | Hughes et al. |
| 2014/0257306 A1 | 9/2014 | Edwards et al. |
| 2015/0088143 A1 | 3/2015 | Lipman et al. |
| 2015/0157341 A1 | 6/2015 | Catanzarite et al. |
| 2017/0027587 A1 | 2/2017 | Fraone et al. |
| 2018/0177512 A1 | 6/2018 | Hogan et al. |
| 2018/0185097 A1 | 7/2018 | Langhorn et al. |
| 2019/0223886 A1 | 7/2019 | Fritzinger |
| 2019/0223887 A1 | 7/2019 | Fritzinger et al. |

FOREIGN PATENT DOCUMENTS

| | | |
|---|---|---|
| CA | 2696584 A1 | 2/2009 |
| CA | 2753485 A1 | 9/2010 |
| CA | 2795724 A1 | 11/2011 |
| EP | 2649951 A2 | 10/2013 |
| EP | 3096693 A1 | 11/2016 |
| FR | 2918554 A1 | 1/2009 |
| WO | 9414366 A2 | 7/1994 |
| WO | 2005084558 A1 | 9/2005 |
| WO | 2008157412 A2 | 12/2008 |
| WO | 2009111639 A1 | 9/2009 |
| WO | 2010121147 A1 | 10/2010 |
| WO | 2011106409 A1 | 9/2011 |
| WO | 2011106430 A1 | 9/2011 |
| WO | 2012024317 A2 | 2/2012 |
| WO | 2015048319 A1 | 4/2015 |
| WO | 2015121400 A1 | 8/2015 |
| WO | 2015185865 A1 | 12/2015 |
| WO | 2017007820 A1 | 1/2017 |

* cited by examiner

CUSTOMIZED PATIENT-SPECIFIC SURGICAL INSTRUMENT SYSTEMS AND METHODS

This application is a continuation application of and claims priority to U.S. patent application Ser. No. 15/878,710, filed Jan. 24, 2018, now U.S. Pat. No. 10,631,878, the entirety of which is expressly incorporated herein by reference.

CROSS-REFERENCE

Cross-reference is made to U.S. patent application Ser. No. 15/878,717, filed Jan. 24, 2018, entitled "METHOD OF DESIGNING AND MANUFACTURING LOW-PROFILE CUSTOMIZED PATIENT-SPECIFIC ORTHOPAEDIC SURGICAL INSTRUMENTS," U.S. patent application Ser. No. 15/878,715, filed Jan. 24, 2018, now U.S. Pat. No. 10,537,343, entitled "LOW-PROFILE METALLIC CUSTOMIZED PATIENT-SPECIFIC ORTHOPAEDIC SURGICAL INSTRUMENTS," and U.S. patent application Ser. No. 16/724,495, filed on Dec. 23, 2019, entitled "LOW-PROFILE METALLIC CUSTOMIZED PATIENT-SPECIFIC ORTHOPAEDIC SURGICAL INSTRUMENTS," the entirety of which are expressly incorporated herein by reference.

TECHNICAL FIELD

The present disclosure relates generally to orthopaedic surgical instruments and, more particularly, to customized patient-specific orthopaedic surgical instruments.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. In a hip replacement surgical procedure, a patient's natural acetabulum is replaced by a prosthetic cup and a patient's natural femoral head is partially or totally replaced by a prosthetic stem and femoral ball.

To facilitate the replacement of the natural joint with a prosthesis, orthopaedic surgeons use a variety of orthopaedic surgical instruments such as, for example, cutting blocks, drill guides, milling guides, and other surgical instruments. Typically, the orthopaedic surgical instruments are reusable and generic with respect to the patient such that the same orthopaedic surgical instrument may be used on a number of different patients during similar orthopaedic surgical procedures.

The orthopaedic surgical instruments may also be customized to a specific patient. Such "customized patient-specific orthopaedic surgical instruments" are single-use surgical tools for use by a surgeon in performing an orthopaedic surgical procedure that is intended, and configured, for use on a particular patient. It should be appreciated that these instruments are distinct from standard, non-patient specific orthopaedic surgical instruments that are intended for use on a variety of different patients. These customized patient-specific orthopaedic surgical instruments are distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

SUMMARY

According to one aspect of the disclosure, an orthopaedic surgical instrument is disclosed. The instrument comprises a metallic customized patient-specific surgical instrument comprising a base plate sized to be positioned on a resected surface of a distal end of a patient's femur. The base plate has a bone-facing surface, a distal surface positioned opposite the bone-facing surface, and an outer wall extending between the bone-facing surface and the distal surface. The metallic customized patient-specific surgical instrument also comprises an anterior resection guide body attached to, and extending from, the distal surface to a free distal end. The anterior resection guide body includes an anterior cutting guide slot sized to receive a cutting saw blade. A posterior resection guide body is attached to, and extending from, the distal surface to a free distal end, and the posterior resection guide body includes a posterior cutting guide slot sized to receive a cutting saw blade. The metallic customized patient-specific surgical instrument also comprises a pair of chamfer resection guide bodies attached to, and extending from, the distal surface. Each chamfer resection guide body includes a chamfer cutting guide slot sized to receive a cutting saw blade, and each chamfer cutting guide slot extends obliquely relative to the other cutting guide slots.

In some embodiments, the metallic customized patient-specific surgical instrument may further comprise a boss attached to, and extending from, the distal surface to a free distal end spaced apart from the free distal end of the body. The boss may include an opening that is defined in its free distal end, and a drill guide slot may extend from the opening in the boss through a second opening defined in the bone-facing surface. The drill guide slot may be sized to receive a surgical drill.

In some embodiments, the bone-facing surface may include a customized patient-specific outer edge that is shaped to match an outer edge of the resected surface of the distal end of the patient's femur.

Additionally, in some embodiments, the metallic customized patient-specific surgical instrument may include a superior notch that is defined by a section of the outer edge, and the anterior cutting guide slot may open into the superior notch.

In some embodiments, the metallic customized patient-specific surgical instrument may include an inferior notch that is defined by a section of the outer edge, and the posterior cutting guide slot may open into the inferior notch.

In some embodiments, the metallic customized patient-specific surgical instrument may include a plurality of laminations of metallic material.

According to another aspect, a method of performing an orthopaedic surgery comprises aligning a customized patient-specific surgical instrument with a resected distal surface of a patient's bone, positioning the customized patient-specific surgical instrument in contact with the resected distal surface, and rotating the customized patient-specific surgical instrument on the resected distal surface to align an outer perimeter edge of the resection distal surface with a customized, patient-specific outer edge of a bone-facing surface of the customized patient-specific surgical instrument, and inserting a cutting saw through a cutting guide slot defined in the customized patient-specific surgical instrument to resect the patient's bone.

In some embodiments, the customized patient-specific surgical instrument used in the method includes an anterior cutting guide slot, a posterior cutting guide slot, and a pair of chamfer cutting guide slots.

According to another aspect, the orthopaedic surgical instrument comprises a metallic customized patient-specific surgical instrument comprising a base plate sized to be positioned on a resected surface of a distal end of a patient's femur. The base plate has a bone-facing surface, a distal surface positioned opposite the bone-facing surface, and an outer wall extending between the bone-facing surface and the distal surface. The metallic customized patient-specific surgical instrument comprises a body attached to, and extending from, the distal surface to a free distal end, and the body includes an elongated opening that is defined in its free distal end. A cutting guide slot extends from the opening in the body through a first opening defined in the bone-facing surface, and the cutting guide slot is sized to receive a cutting saw blade. A boss is attached to, and extends from, the distal surface to a free distal end spaced apart from the free distal end of the body. The boss includes an opening that is defined in its free distal end. The metallic customized patient-specific surgical instrument also comprises a drill guide slot extending from the opening in the boss through a second opening defined in the bone-facing surface. The drill guide slot is sized to receive a surgical drill.

In some embodiments, the bone-facing surface may include a customized patient-specific outer edge that is shaped to match an outer edge of the resected surface of the distal end of the patient's femur.

Additionally, in some embodiments, the metallic customized patient-specific surgical instrument may include a notch that is defined by a section of the outer edge, and the cutting guide slot may open into the notch. In some embodiments, the section of the outer edge may be a superior section such that the notch is defined at a superior end of the metallic customized patient-specific surgical instrument.

In some embodiments, the section of the outer edge may be an inferior section such that the notch is defined at an inferior end of the metallic customized patient-specific surgical instrument.

In some embodiments, the body may be a first body, the cutting guide may be a first cutting guide, and the metallic customized patient-specific surgical instrument may further comprise a second body attached to, and extending from, the distal surface to a distal end spaced apart from the distal ends of the first body and the boss. The second body may include an elongated opening that is defined in its distal end. A second cutting guide slot may extend from the opening in the second body through a third opening defined in the bone-facing surface. The second cutting guide slot may be sized to receive a cutting saw blade.

In some embodiments, the first cutting guide may define a first cutting plane, and the second cutting guide may define a second cutting plane that is angled relative to the first cutting plane. Additionally, in some embodiments, the metallic customized patient-specific surgical instrument may further comprise a third body attached to, and extending from, the distal surface to a distal end attached to the distal end of the second body. The third body may include an elongated opening that is defined in its distal end. A third cutting guide slot may extend from the opening in the third body through a fourth opening defined in the bone-facing surface. The third cutting guide slot may be sized to receive a cutting saw blade and may intersect the second cutting guide slot.

In some embodiments, the third cutting guide may define a third cutting plane that is angled relative to the first cutting plane and the second cutting plane. Additionally, in some embodiments, a passageway may be defined between a surface of the second body, a surface of the third body, and the distal surface of the base plate.

In some embodiments, the metallic customized patient-specific surgical instrument may further comprise a fourth body attached to, and extending from, the distal surface to a free distal end spaced apart from the distal ends of the first, second, and third bodies. The fourth body may include an elongated opening that is defined in its distal end, and a fourth cutting guide slot may extending from the opening in the fourth body through a fifth opening defined in the bone-facing surface. The fourth cutting guide slot may be sized to receive a cutting saw blade and crossing the second cutting guide slot.

In some embodiments, the metallic customized patient-specific surgical instrument may include a plurality of laminations of metallic material.

It should also be appreciated that in some embodiments a metallic customized patient-specific surgical instrument comprises a base plate sized to be positioned on a resected surface of a distal end of a patient's femur. The base plate has a bone-facing surface, a distal surface positioned opposite the bone-facing surface, and an outer wall extending between the bone-facing surface and the distal surface. The metallic customized patient-specific surgical instrument also comprises an anterior resection guide body attached to, and extending from, the distal surface to a free distal end. The anterior resection guide body includes an anterior cutting guide slot sized to receive a cutting saw blade. A posterior resection guide body is attached to, and extending from, the distal surface to a free distal end, and the posterior resection guide body includes a posterior cutting guide slot sized to receive a cutting saw blade. The metallic customized patient-specific surgical instrument also comprises a pair of chamfer resection guide bodies attached to, and extending from, the distal surface. Each chamfer resection guide body includes a chamfer cutting guide slot sized to receive a cutting saw blade, and each chamfer cutting guide slot extends obliquely relative to the other cutting guide slots.

In some embodiments, the metallic customized patient-specific surgical instrument may further comprise a boss attached to, and extending from, the distal surface to a free distal end spaced apart from the free distal end of the body. The boss may include an opening that is defined in its free distal end, and a drill guide slot may extend from the opening in the boss through a second opening defined in the bone-facing surface. The drill guide slot may be sized to receive a surgical drill.

In some embodiments, the bone-facing surface may include a customized patient-specific outer edge that is shaped to match an outer edge of the resected surface of the distal end of the patient's femur.

Additionally, in some embodiments, the metallic customized patient-specific surgical instrument may include a superior notch that is defined by a section of the outer edge, and the anterior cutting guide slot may open into the superior notch.

In some embodiments, the metallic customized patient-specific surgical instrument may include an inferior notch that is defined by a section of the outer edge, and the posterior cutting guide slot may open into the inferior notch.

In some embodiments, the metallic customized patient-specific surgical instrument may include a plurality of laminations of metallic material.

It should also be appreciated that in some embodiments a method of performing an orthopaedic surgery comprises aligning a customized patient-specific surgical instrument with a resected distal surface of a patient's bone, positioning the customized patient-specific surgical instrument in contact with the resected distal surface, and rotating the customized patient-specific surgical instrument on the resected distal surface to align an outer perimeter edge of the resection distal surface with a customized, patient-specific outer edge of a bone-facing surface of the customized patient-specific surgical instrument, and inserting a cutting saw through a cutting guide slot defined in the customized patient-specific surgical instrument to resect the patient's bone.

In some embodiments, the customized patient-specific surgical instrument used in the method includes an anterior cutting guide slot, a posterior cutting guide slot, and a pair of chamfer cutting guide slots.

BRIEF DESCRIPTION OF THE DRAWINGS

The detailed description particularly refers to the following figures, in which.

DETAILED DESCRIPTION OF THE DRAWINGS

Figure 1:
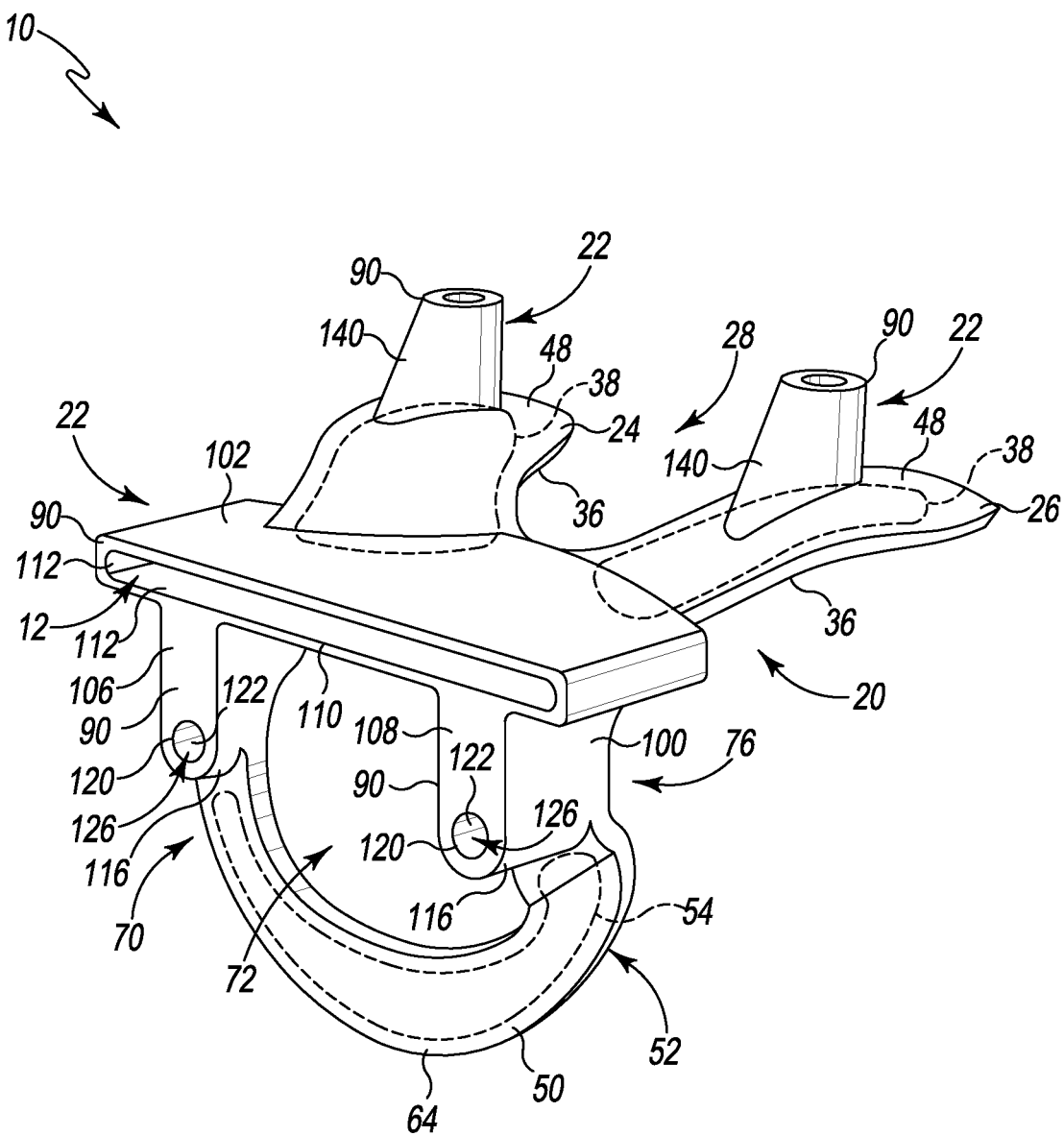
FIG. 1 is a perspective view of a customized patient-specific orthopaedic femoral cutting block.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Referring to FIGS. 1-10, a customized patient-specific orthopaedic surgical instrument 10 is shown. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments (i.e., "patient-universal instruments" such as patient-universal cutting blocks) that are intended for use on a variety of different patients and were not fabricated or customized to any particular patient. Additionally, it should be appreciated that, as used herein, the term "customized patient-specific orthopaedic surgical instrument" is distinct from orthopaedic prostheses or implants, whether patient-specific or generic, which are surgically implanted in the body of the patient. Rather, an orthopaedic surgeon uses customized patient-specific orthopaedic surgical instruments to assist in the implantation of orthopaedic prostheses. Examples of "customized patient-specific orthopaedic surgical instruments" include customized patient-specific drill/pin guides, customized patient-specific tibial cutting blocks, customized patient-specific femoral cutting blocks, and customized patient-specific alignment guides. The surgical instrument 10 shown in FIGS. 1-10 is one embodiment of a customized patient-specific femoral cutting block including a cutting guide slot 12 positioned to guide a customized, patient-specific resection of a distal end 14 of a patient's femur 16 (see FIGS. 6-7) along a predetermined resection plane. As described in greater detail below, the femoral cutting block 10 is configured to be coupled to the patient's femur 16 in a unique pre-determined location and orientation. In the illustrative embodiment, the structure of the cutting block 10 has been contoured to reduce its size relative to conventional cutting blocks and avoid contact with undesirable regions of the patient's bone.

As shown in FIG. 1, the femoral cutting block 10 includes a base plate 20 and a number of surgical tool guide bodies 22 that are attached to, and extend outwardly from, the base plate 20. In the illustrative embodiment, the femoral cutting block 10 is a single monolithic component formed from a metallic material such as, for example, stainless steel. In that way, the base plate 20 and the guide bodies 22 form a single monolithic metallic block. As described in greater detail below, the femoral cutting block 10 is formed by Direct Metal Laser Sintering (DMLS), also known as Selective Laser Sintering (SLS), which is a form of 3-D printing technology. In DMLS, the femoral cutting block 10 is formed in a layer-by-layer fashion using laser sintering in which light fuses metallic powder, forming the metallic structures that define the femoral cutting block 10. It should be appreciated that other forms of 3-D printing technology such as, for example, optical fabrication, photo-solidification, or resin printing may be used to fabricate the femoral cutting block 10.

The base plate 20 includes a pair of arms 24, 26 that are configured to engage the distal end 14 of the patient's femur 16. The arms 24, 26 are spaced apart from each other such that a notch 28 is defined between the inner edges of the arms 24, 26. The notch 28 is sized and shaped to correspond to the natural intercondylar notch 30 (see FIG. 12) of the patient's femur 16, which is defined between the natural condyles 32, 34 of the patient's femur. In that way, contact within bone surfaces with the natural intercondylar notch 30, which may be difficult to model, is avoided.

As shown in FIGS. 1-4, each of the arms 24, 26 has a bone-contacting or bone-facing surface 36 that engages one of the natural condyles 32, 34. In the illustrative embodiment, each bone-facing surface 36 includes a number of negative contours 38 that are configured to receive a portion of the natural condyles 32, 34. As shown in, for example, FIGS. 2, 4, and 6-8, each contour 38 has a unique set of ridges 40 and depressions 42 that are shaped to engage a corresponding unique set of depressions 44 and ridges 46 of the natural condyles 32, 34. Each of the arms 24, 26 also includes an outer surface 48 that is positioned opposite its corresponding bone-facing surface 36. In the illustrative embodiment, each outer surface 48 is substantially smooth. As used herein, the term "substantially" should be understood to refer to permit the normal tolerances created by manufacturing variation and other design criteria. As such, a "substantially smooth surface" is one that is smooth within the normal tolerances created or permitted by manufacturing variation and other design criteria.

As shown in FIG. 1, the base plate 20 also includes an anterior flange 50 that is configured to engage the distal end 14 of the patient's femur 16. The anterior flange 50 includes a bone-facing surface 52 that includes a number of negative contours 54 that are configured to receive a portion of the patient's femur 16. As shown in, for example, FIGS. 2, 4, and 8, the contour 54 of the anterior flange 50 has a unique set of ridges 56 and depressions 58 that are shaped to engage a corresponding unique set of depressions 60 and ridges 62 of the patient's femur 16. The anterior flange 50 also includes an outer surface 64 that is positioned opposite the bone-facing surface 52. In the illustrative embodiment, the outer surface 64 is substantially smooth.

The negative contours 38, 54 of the base plate 20 permit the cutting block 10 (and hence the tool guide bodies) to be positioned on the patient's femur 16 in a unique pre-determined location and orientation. As shown in FIGS. 4 and 6-8, the bone-facing surface 52 includes a pair of curved posterior edges 66, 68 that define a portion of the contour 54 and are shaped to match a portion of the patient's femur. As a result, each of the edges 66, 68 includes convex and concave portions to receive corresponding concave and convex portions of the patient's femur. The edge 66 includes a posterior tip 69 that is sized and shaped to be positioned in the patient's natural trochlear groove 166.

Figure 2:
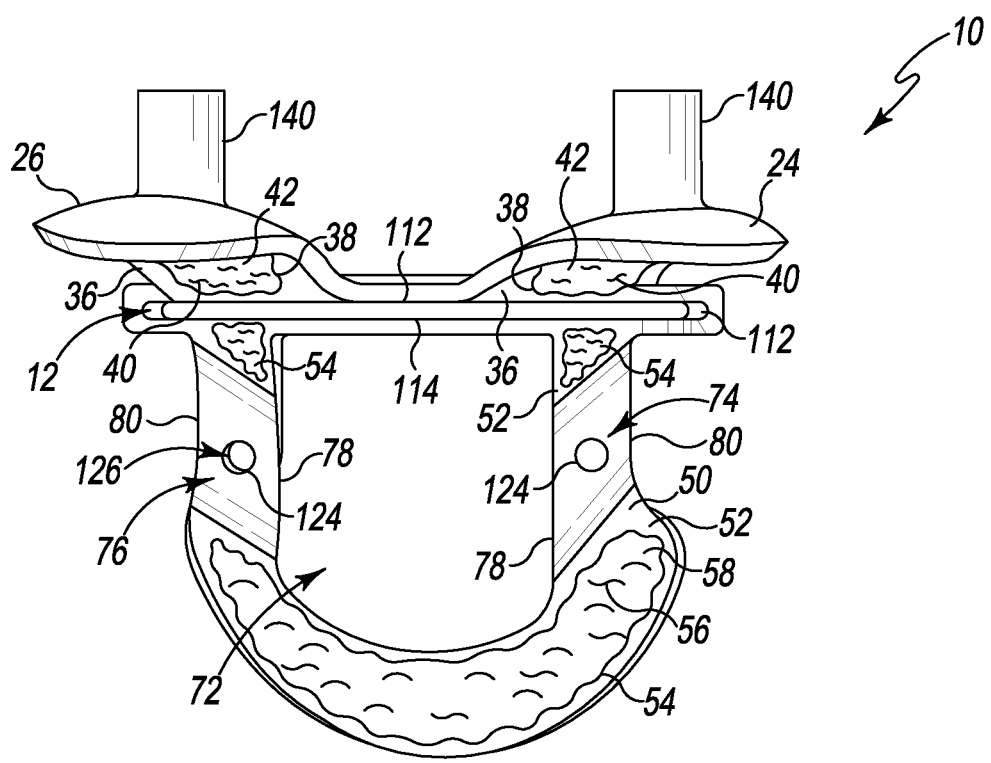
FIG. 2 is a posterior side elevation view of the cutting block of FIG. 1.
Figure 3:
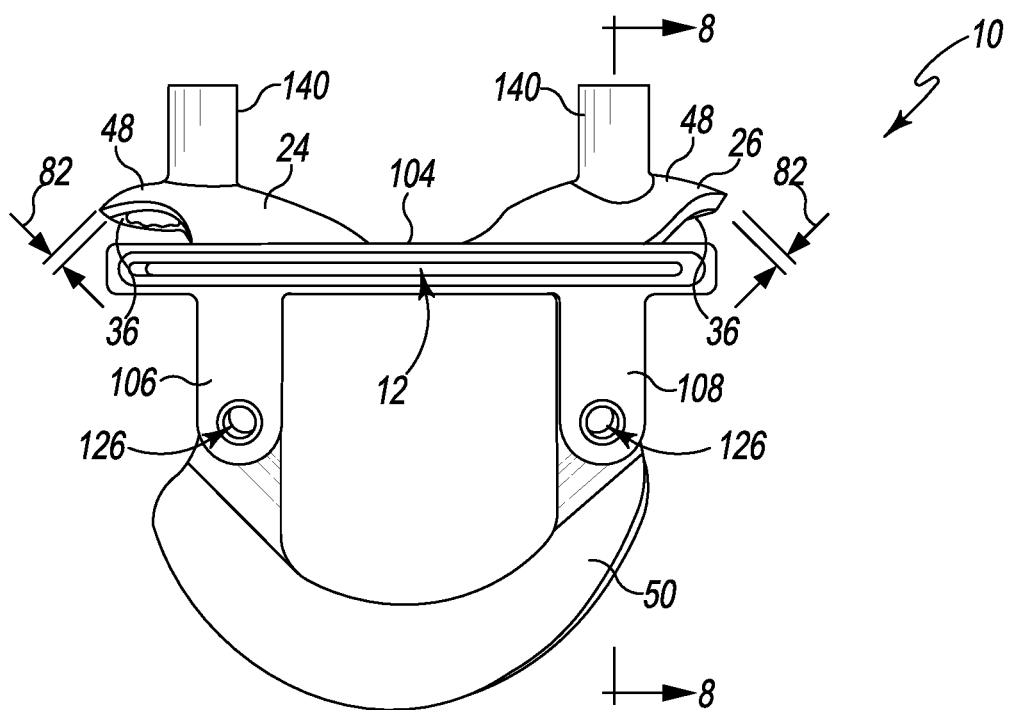
FIG. 3 is an anterior side elevation view of the cutting block of FIG. 1.

The base plate 20 also includes a number of customized cavities 70, which are sized to be positioned over regions in the pre-determined location of the bone that may include a defect or are damaged or difficult to model. In that way, the cavities 70 are sized such that contact with those regions may be avoided so as to not interfere with positioning the cutting block 10 in the pre-determined location and orientation. In the illustrative embodiment, the notch 28 defined between the arms 24, 26 is one of the customized cavities. As shown in FIGS. 1-3, the customized cavities 70 also include an aperture 72 that extends through the bone-facing surface 52 of the anterior flange 50. As shown in FIG. 2, the customized cavities 70 also include a pair of channels 74, 76 that are defined in the bone-facing surface 52 of the anterior flange 50. In the illustrative embodiment, each channel 74, 76 extends from an end 78 that opens into the aperture 72 to an open end 80 that is defined in the outer edge of the anterior flange 50.

Figure 4:
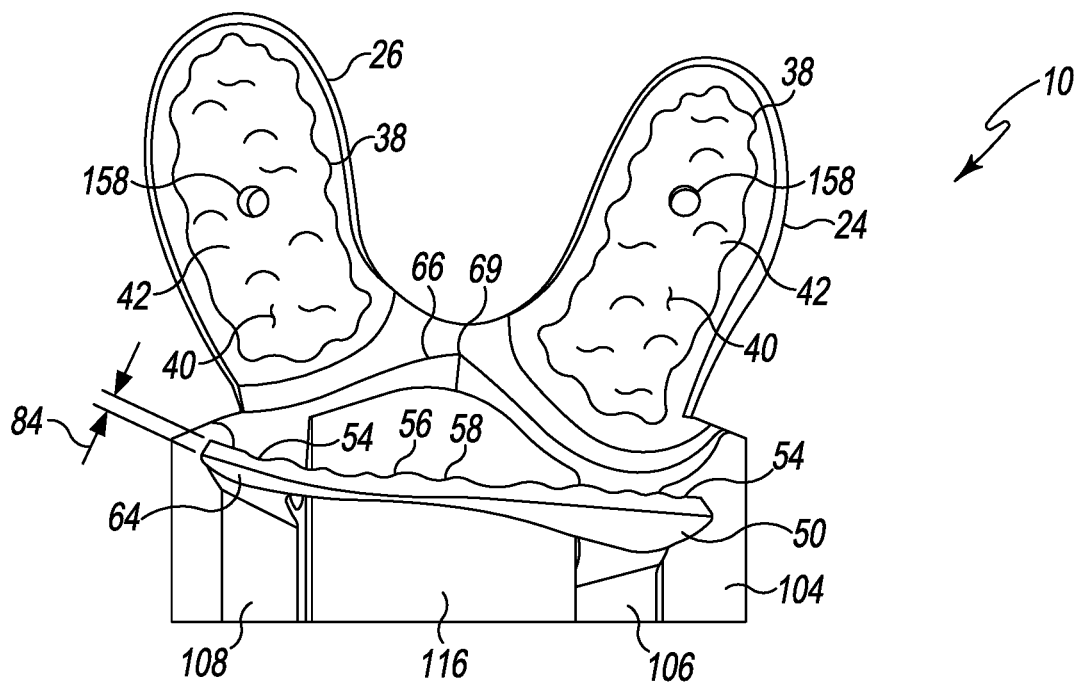
FIG. 4 is a proximal plan view of the cutting block of FIG. 1.
Figure 5:
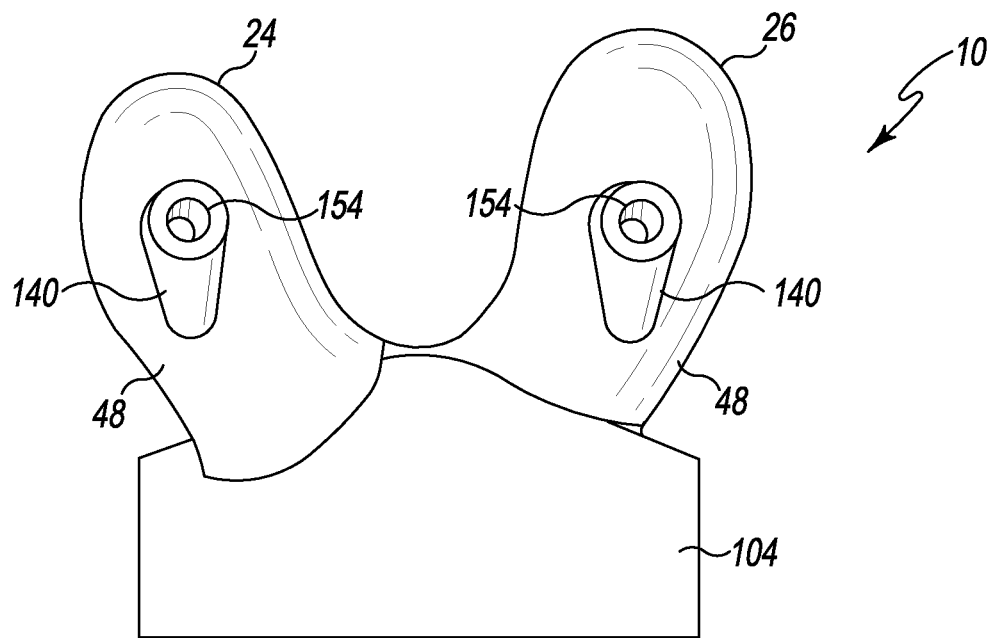
FIG. 5 is a distal plan view of the cutting block of FIG. 1.
Figure 6:
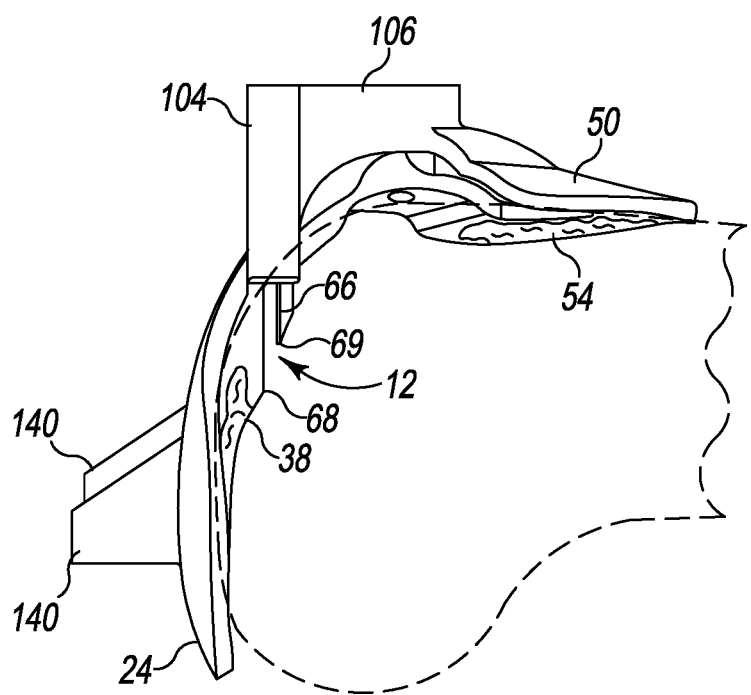
FIG. 6 is a side elevation view of the cutting block of FIG. 1 shown positioned relative to a distal end of a patient's femur.
Figure 7:
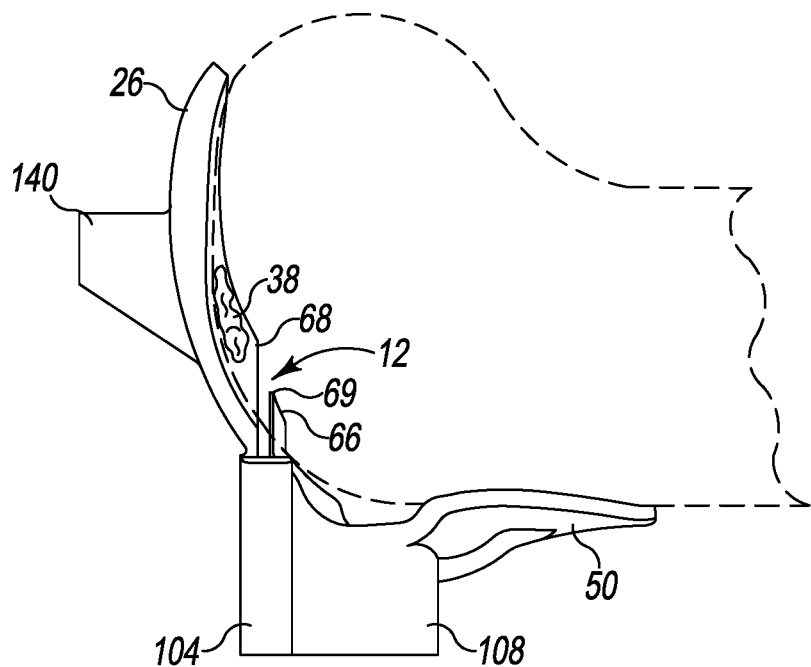
FIG. 7 is another side elevation view of the cutting block of FIG. 1 shown positioned relative to the distal end of the patient's femur.

In the illustrative embodiment, the base plate 20 of the cutting block 10 has a low-profile to reduce the size of the incision and reduce the amount of bone displacement needed to position the cutting block 10. The low-profile has been customized for block 10 by minimizing the thicknesses of the arms 24, 26 and the anterior flange 50. As shown in FIG. 3, a thickness 82 is defined between the outer surface 48 and the bone-facing surface 36 of each arm. To minimize the thickness 82, the outer surface 48 of each arm is convexly curved to follow the concave curvature of the bone-facing surface 36. Similarly, as shown in FIG. 4, a thickness 84 is defined between the outer surface 64 and the bone-facing surface 52 of the anterior flange 50, and the outer surface 64 of the flange 50 is shaped to follow the geometry of the bone-facing surface 52 to minimize the thickness 84.

As shown in FIGS. 1-8, each of the surgical tool guide bodies 22 of the cutting block 10 is attached to and extends outwardly from the outer surfaces 48, 64 of the arms 24, 26 and the anterior flange 50 to a free end 90 that is spaced apart from the base plate 20. In the illustrative embodiment, the guide bodies 22 include an anterior guide body 100 that extends anteriorly from the anterior ends of the arms 24, 26 and the anterior flange 50 to its free end 102. The anterior guide body 100 includes a distal flange 104 and a pair of bosses 106, 108 that extend proximally from the flange 104. As shown in FIG. 1, the aperture 72 defined in the base plate 20 is positioned proximal of the distal flange 104 and between the bosses 106, 108.

The distal flange 104 of the anterior guide body 100 includes an elongated opening 110 that is defined in the free end 102 and a number of inner walls 112 that extend inwardly from the opening 110. As shown in FIG. 2, the inner walls 112 extend to another opening 114 that is defined in the bone-facing surface 52. As shown in FIGS. 4 and 6-8, the opening 114 extends through the contour 54 of the base plate 20 such that the opening 114 is defined by edges 66, 68 of the bone-facing surface 52, which follow a curved, irregular path that matches the shape of the patient's femur 16 in that region. The opening 114 cooperates with the inner walls 112 and the elongated opening 110 to define the guide slot 12, which is sized and shaped to guide a surgical tool such as, for example, a cutting blade, into engagement with the patient's bone. As described above, the cutting guide slot 12 is positioned to guide a customized, patient-specific resection of a distal end 14 of a patient's femur 16. Because the edge 66 follows the shape of the patient's femur and the posterior tip of the edge 66 extends into the patient's trochlear groove, the cutting guide slot 12 provides support for the cutting blade in close proximity to the region under resection.

As shown in FIG. 1, each of the bosses 106, 108 extend from a proximal surface 116 of the distal flange 104 to a curved proximal end 118. It should be appreciated that in other embodiments one or both of the bosses 106, 108 may be spaced apart from the distal flange 104, thereby forming separate guide bodies. An opening 120 is defined in the free end 102 of each of the bosses 106, 108 adjacent to the proximal end 118. An inner wall 122 extends inwardly from the opening 120. As shown in FIG. 2, each inner wall 122 extends to another opening 124 that opens into one of the channels 74, 76 to define a guide slot 126 extending through the cutting block 10. In the illustrative embodiment, each guide slot 126 is a drill guide and fixation pin guide hole, which is sized and shaped to guide a surgical drill to prepare the patient's bone to receive a fixation pin to couple to the block 10 to the bone.

Figure 9:
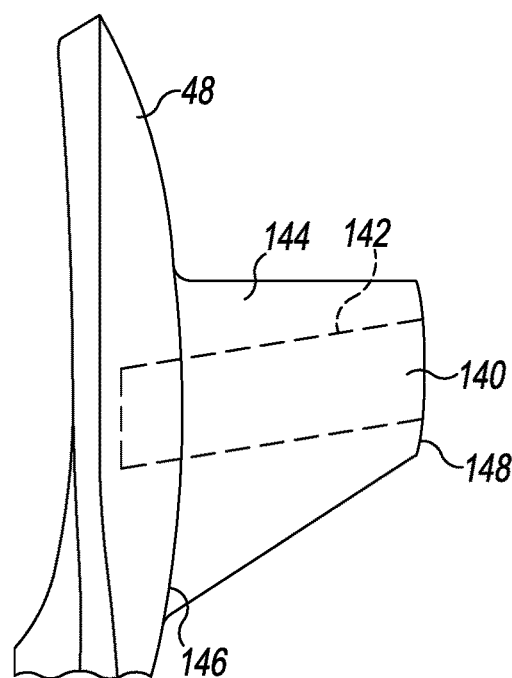
FIG. 9 is a side elevation view of a guide pin body of the cutting block of FIG. 1.
Figure 10:
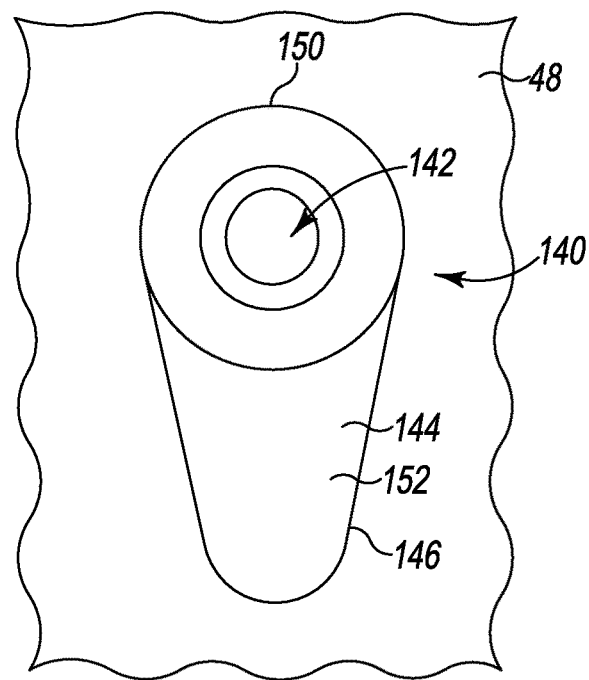
FIG. 10 is a distal plan view of the guide pin body of FIG. 9.

Referring now to FIGS. 9-10, the guide bodies 22 include a pair of posterior guide bosses 140, which are attached to, and extend distally from, the outer surfaces 48 of the arms 24, 26, respectively. Each posterior guide boss 140 includes a guide slot 142 that is sized and shaped to guide surgical drill and a fixation pin into engagement with the patient's bone to couple to the block 10 to the bone. Each guide boss 140 includes a post 144 that extends from a base 146 attached to the outer surface 48 of one of the arms 24, 26 to a free end 148 that is spaced apart from the outer surface 48.

As shown in FIGS. 9 and 10, the base 146 is wider in the anterior-posterior direction than the free end 148. Each post 144 also includes a convex curved posterior surface 150 that extends substantially orthogonal to the arm outer surface 48. In the illustrative embodiment, each post 144 also includes a curved tapered anterior surface 152 that extends obliquely relative to the arm outer surface 48. The curved tapered anterior surface 152 improves the manufacturability of the cutting block 10 by eliminating a flat, horizontal surface, which, during fabrication, would face downward and require a support structure.

Returning to FIG. 8, an opening 154 is defined in the free end 148 of each boss 140. An inner wall 156 extends inwardly from the opening 154 to another opening 158 that is defined in a bone-facing surface 36 of one of the arms 24, 26. The openings 154, 158 and inner wall 156 cooperate to define the guide slot 142. As described above, each guide slot 142 is a drill guide and fixation pin guide hole, which is sized and shaped to guide a surgical drill or self-drilling fixation pin to prepare the patient's bone to receive a fixation pin to couple to the block 10 to the bone.

Figure 8:
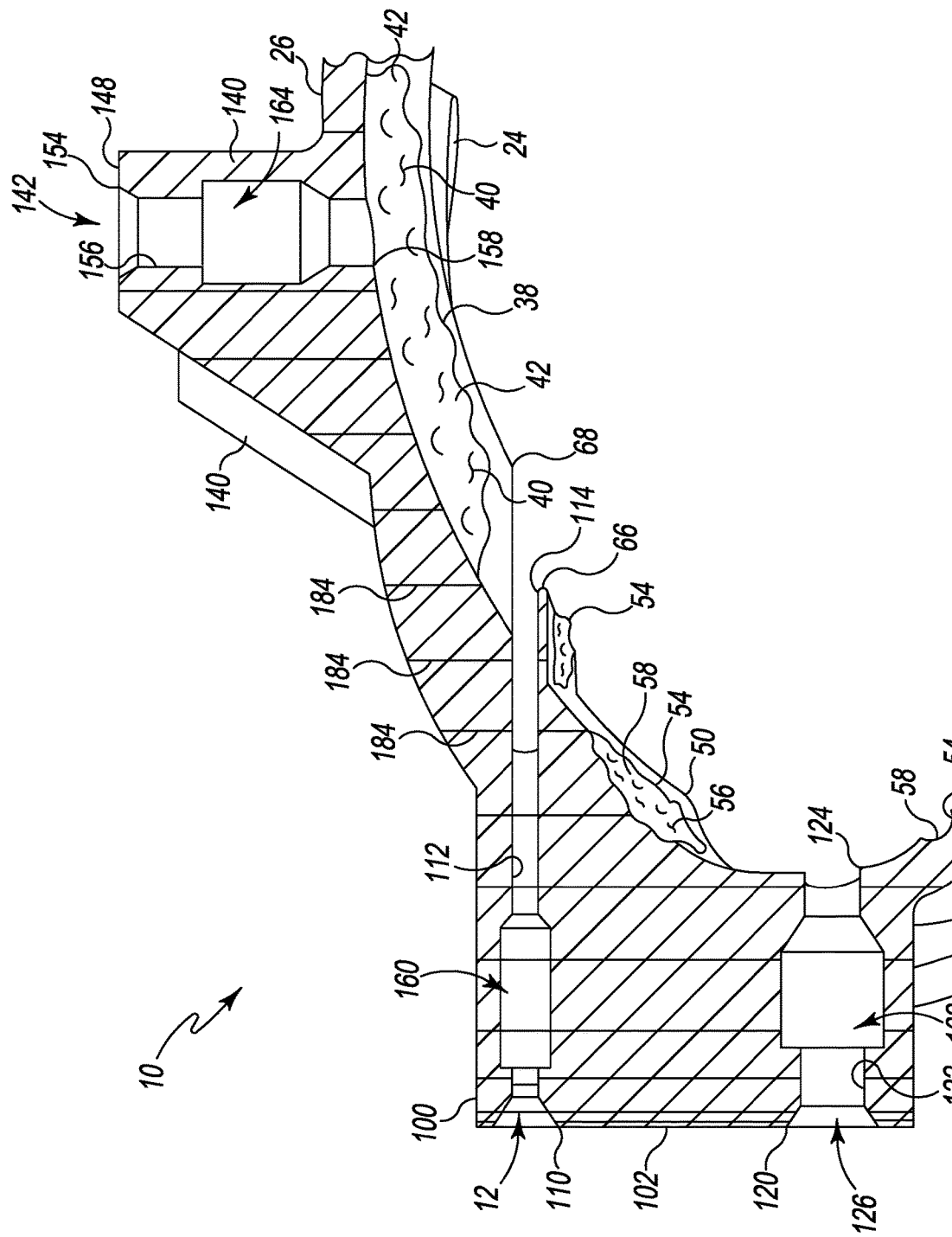
FIG. 8 is a cross-sectional elevation view taken along the line 8-8 in FIG. 3.

As shown in FIG. 8, the inner walls 112, 122, 156 define a number of relief sections 160, 162, 164 in the guide slots 12, 126, 142, respectively, of the cutting block 10. Each of the relief sections 160, 162, 164 is larger (e.g., wider) than the rest of the guide slots 12, 126, 142 to improve manufacturability.

Figure 11A:
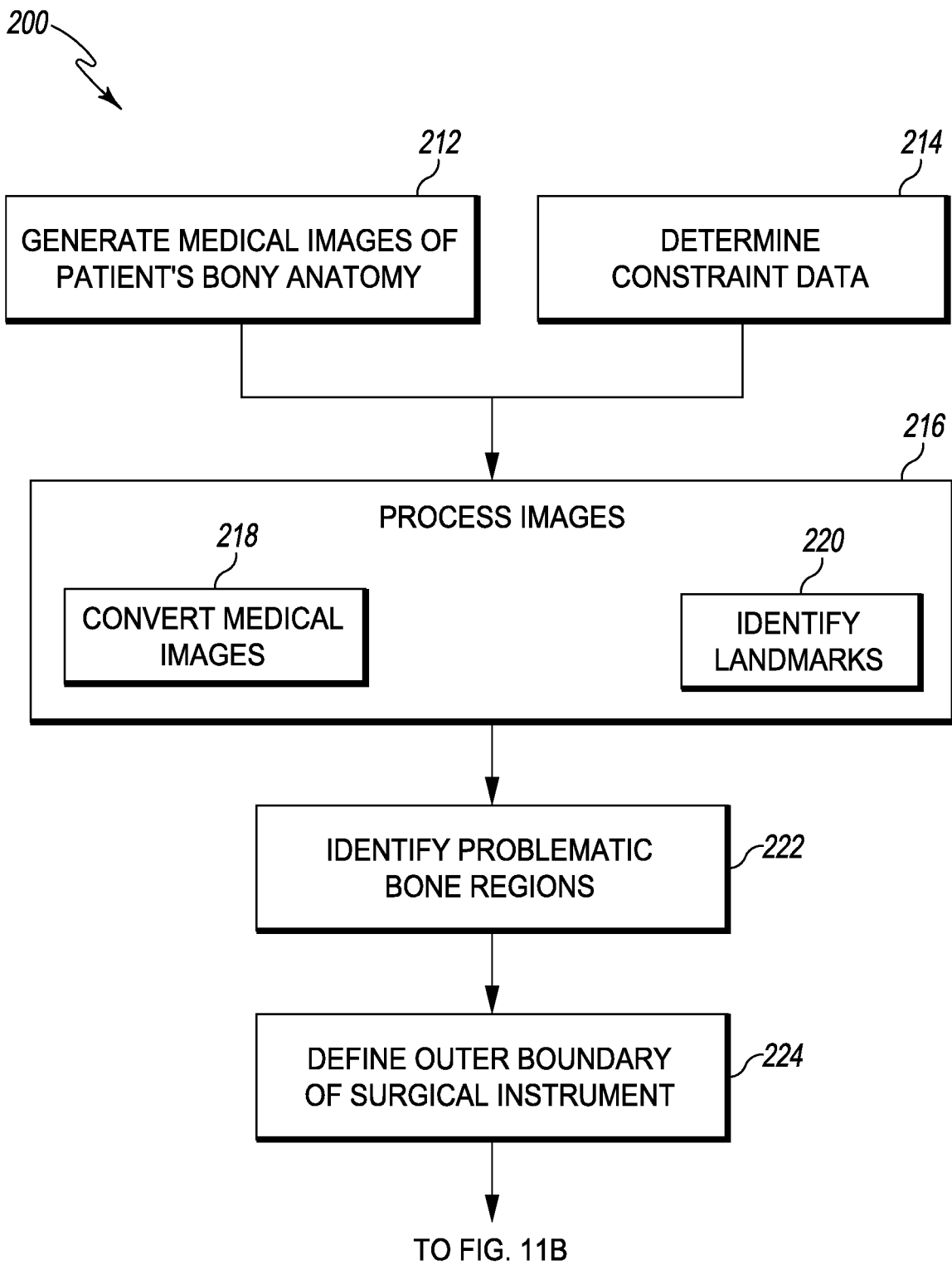
FIGS. 11A-B are a simplified flow diagram of a process of designing and fabricating the cutting block of FIG. 1.
Figure 11B:
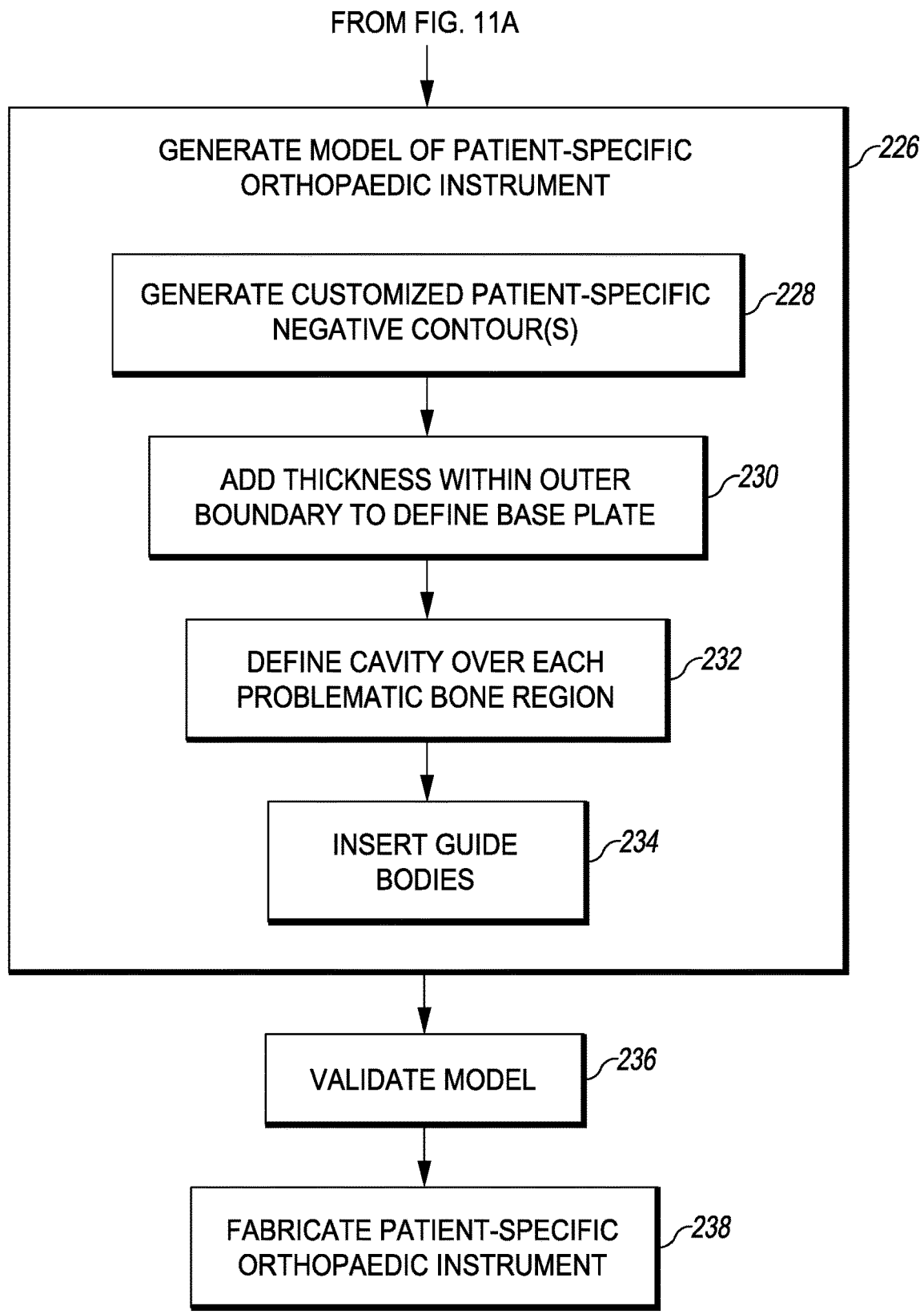

Referring now to FIGS. 11A-B, a routine 200 for fabricating the customized patient-specific orthopaedic surgical instrument 10 is illustrated. The method 200 includes process steps 212 and 214, in which an orthopaedic surgeon performs pre-operative planning of the orthopaedic surgical procedure to be performed on a patient. The process steps 212 and 214 may be performed in any order or contemporaneously with each other. In process step 212, a number of medical images of the relevant portions of a patient's bone are generated. For example, for a knee replacement surgery, the medical images may include images of the distal end of a patient's femur and the proximal end of a patient's tibia. For a hip replacement surgery, the medical images may include images of the patient's acetabulum and surrounding bony anatomy, as well as images of the proximal end of the patient's femur. To do so, the orthopaedic surgeon or other healthcare provider may operate an imaging system to generate the medical images. The medical images may be embodied as any number and type of medical images capable of being used to generate a three-dimensional rendered model of the patient's acetabulum and surrounding bony anatomy. For example, the medical images may be embodied as any number of computed tomography (CT) images, magnetic resonance imaging (MRI) images, or other three-dimensional medical images. Additionally, or alternatively, as discussed in more detail below in regard to process step 216, the medical images may be embodied as a number of X-ray images or other two-dimensional images from which a three-dimensional rendered model of the relevant area of the patient's bone.

In process step 214, the orthopaedic surgeon may determine any additional pre-operative constraint data. The constraint data may be based on the orthopaedic surgeon's preferences, preferences of the patient, anatomical aspects of the patient, guidelines established by the healthcare facility, or the like. For example, in a knee replacement surgery, the constraint data may include the type and size of the knee prosthesis, the amount of distal and posterior resections to be performed on the patient's femur and so forth. In a hip replacement surgery, the constraint data may include the orthopaedic surgeon's preference for the amount of inclination and version for an acetabular prosthesis, the amount of the bone to ream, the size range of the orthopaedic implant, and/or the like. In some embodiments, the orthopaedic surgeon's preferences are saved as a surgeon's profile, which may be used as a default constraint values for further surgical plans.

The medical images and the constraint data, if any, may be transmitted or otherwise provided to an orthopaedic surgical instrument vendor or manufacturer for processing the images. The orthopaedic surgical instrument vendor or manufacturer processes the medical images in step 216 to facilitate the determination of the proper resection planes, instrument location, implant sizing, and fabrication of the customized patient-specific orthopaedic surgical instrument as discussed in more detail below. The images may also be processed on-site at the hospital, for example, or the surgeon's offices.

In process step 218, three-dimensional images may be converted or otherwise generated from the medical images. For example, in embodiments wherein the medical images are embodied as a number of two-dimensional images, the vendor may use a suitable computer algorithm to generate one or more three-dimensional images form the number of two-dimensional images. Additionally, in some embodiments, the medical images may be generated based on an established standard such as the Digital Imaging and Communications in Medicine (DICOM) standard. In such embodiments, an edge-detection, thresholding, watershed, or shape-matching algorithm may be used to convert or reconstruct images to a format acceptable in a computer aided design application or other image processing application.

In process step 220, the medical images, and/or the converted/reconstructed images from process step 218 may be processed, to determine a number of aspects related to the bony anatomy of the patient such as the anatomical axis of the patient's bones, the mechanical axis of the patient's bone, other axes and various landmarks, and/or other aspects of the patient's bony anatomy. Any suitable algorithm may be used to process the images. In some embodiments, a three-dimensional model of the patient's bone including a three-dimensional rendering of the bone may be generated from the processed images. One such three-dimensional bone model is the femoral bone model 170 is shown in FIGS. 12-15, which are referenced below.

Figure 12:
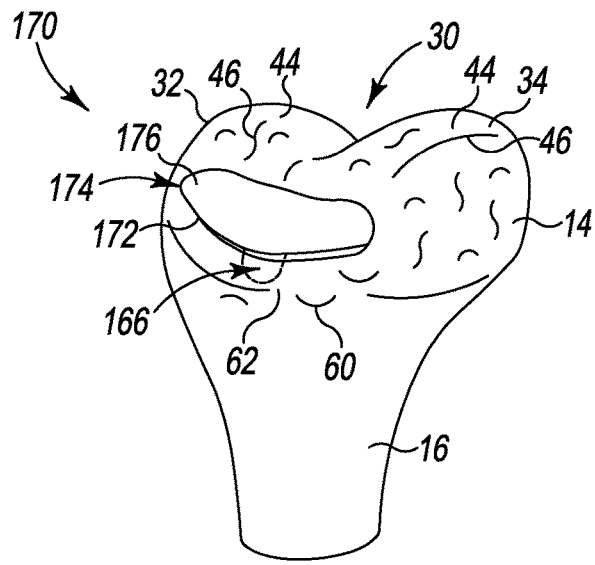
FIGS. 12-15 illustrate some of the steps of the process outlined in FIGS. 11A-B.

In process step 222, a surgeon, vendor, or other user may identify one or more problematic regions of the bone to avoid using the three-dimensional model. Such regions may include osteophytes, damaged regions of the bone, undercuts that would cause the instrument to get stuck on the bone, or other regions that are known to be difficult to model based on the medical images. One such region may include a portion of the patient's trochlear groove. As shown in FIG. 12, the user may outline an outer edge 172 of one such region 174 on the distal end 14 of a patient's femur 16 using the femoral bone model 170. The user may also create a raised or offset surface 176 within the outer edge 172 to define a desired location of a cavity 70 of the orthopaedic surgical instrument.

Figure 13:
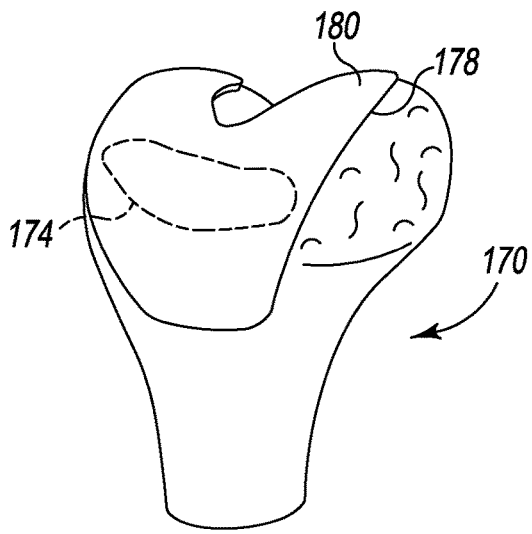

The routine 200 may advance to process step 224 in which an outer boundary 178 of the patient-specific orthopaedic surgical instrument is defined on the femoral bone model 170. As shown in FIG. 13, the outer boundary 178 defines the outer edge of the planned surgical instrument, which may be, for example, the femoral cutting block 10 described above. The boundary 178 identifies the locations and shapes of the arms 24, 26 as well as the location and shape of the anterior flange 50 of the base plate 20 of the cutting block 10.

In process step 226, a model of the customized patient-specific orthopaedic surgical instrument is generated. In some embodiments, the model is embodied as a three-dimensional rendering of the customized patient-specific orthopaedic surgical instrument. In other embodiments, the model may be embodied as a mock-up or fast prototype of the customized patient-specific orthopaedic surgical instrument. The patient-specific orthopaedic surgical instrument to be modeled and fabricated may be determined based on the orthopaedic surgical procedure to be performed, the constraint data, and/or the type of orthopaedic prosthesis to be implanted in the patient.

The particular shape of the customized patient-specific orthopaedic surgical instrument is determined based on the planned location and implantation angles of the orthopaedic prosthesis relative to the patient's bone. Additionally, the planned location of the orthopaedic surgical instrument may be based on the identified landmarks of the patient's bone identified in process step 220.

In some embodiments, the particular shape or configuration of the customized patient-specific orthopaedic surgical instrument may be determined based on the planned location of the instrument relative to the patient's bony anatomy. That is, the customized patient-specific orthopaedic surgical instrument may include a bone-facing surface having a negative contour that matches the corresponding contour of a portion of the bony anatomy of the patient such that the orthopaedic surgical instrument may be coupled to the bony anatomy of the patient in a unique location, which corresponds to the pre-planned location for the instrument. Such negative contours may include a unique set of ridges and depressions shaped to match a corresponding set of ridges and depressions on the patient' bone. When the orthopaedic surgical instrument is coupled to the patient's bony anatomy in the unique location, one or more guides (e.g., cutting or drilling guide) of the orthopaedic surgical instrument may be aligned to the inclination and version planes, as discussed above.

The process sub-steps 228-234 shown in FIG. 11B outline an exemplary sub-routine that may be followed to generate the model of the patient-specific orthopaedic surgical instrument. In process sub-step 228, the femoral bone model 170 may be used to generate the customized patient-specific negative contour or contours of the patient-specific surgical instrument. To do so, the user may create an infinitely thin sheet 180 within the boundary 178 shown in FIG. 13. The thin sheet 180 may include the depressions and ridges to be included in the negative contour of the patient-specific surgical instrument.

In process sub-step 230, the user may add thickness to the sheet 180 within the boundary 178 to generate the outer surface of the customized patient-specific surgical instrument and thereby define the base plate of the instrument. As discussed above, the user may minimize the thickness of the instrument to reduce the size of the incision necessary to place the instrument on the patient's bone. In process sub-step 232, the user may define a cavity 70 over each of the problematic regions 174 identified in process step 222. As part of defining the cavity or cavities, the user may adjust the shape and size of the planned base plate to adjust the planned size and/or weight of the instrument. Each cavity may have an outer edge that is aligned with the edge 172 of the region 174.

Figure 15:
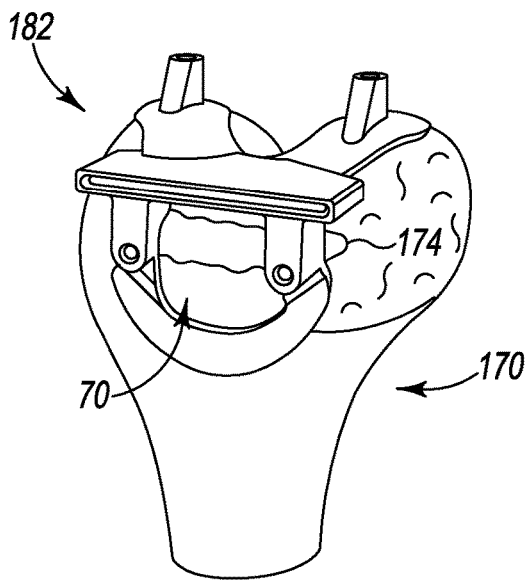

In process sub-step 234, the user may position the surgical instrument guide bodies in position on the femoral bone model 170 to create the model 182 of the patient-specific orthopaedic surgical instrument shown in FIG. 15. To do so, the desired cutting planes for implantation of the orthopaedic prosthesis may be determined. The planned cutting planes may be determined based on the type, size, and position of the orthopaedic prosthesis to be used during the orthopaedic surgical procedure; the process images, such as specific landmarks identified in the images; and the constraint data supplied by the orthopaedic surgeon in process steps 212 and 214. The type and/or size of the orthopaedic prosthesis may be determined based on the patient's anatomy and the constraint data. For example, the constraint data may dictate the type, make, model, size, or other characteristic of the orthopaedic prosthesis. The selection of the orthopaedic prosthesis may also be modified based on the medical images such that an orthopaedic prosthesis that is usable with the bone of the patient and that matches the constraint data or preferences of the orthopaedic surgeon is selected.

Figure 14:
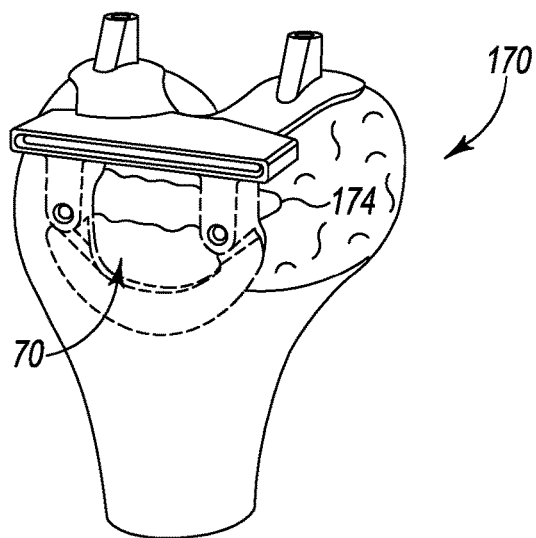

When positioning the guide bodies on the femoral bone model 170, the user may adjust the size, shape, and location of each guide body as needed. As shown in FIGS. 14-15, the user may include a cutting guide slot and one or more drill guide slots for preparing the patient's bone to receive a fixation pin. The orientation of the drill guide slots may be based on the planned resection planes and may be adjusted to facilitate the resection of the patient's bone. As shown in FIGS. 14-15, the guide bodies for the guide slots may be formed by extending the bodies outwardly from the outer surface of the model 182 to their free ends.

It should be appreciated that the sub-steps 228, 230, 232, 234 may be performed in an order different from that described above. For example, a user may choose to identify the planned resection plane first and insert the cutting guide body into the femoral bone model prior to generating the customized patient-specific negative contour. Additionally, in some embodiments, one or more of the sub-steps may be omitted.

After the model of the customized patient-specific orthopaedic surgical instrument has been generated in process step 226, the model is validated in process step 236. The model may be validated by, for example, analyzing the rendered model while coupled to the three-dimensional model of the patient's anatomy to verify the correlation of cutting guides, reaming guides, inclination and version planes, and/or the like. Additionally, the model may be validated by transmitting or otherwise providing the model generated in step 226 to the orthopaedic surgeon for review.

After the model has been validated in process step 236, the customized patient-specific orthopaedic surgical instrument is fabricated in process step 238. As described above, the customized patient-specific orthopaedic surgical instrument may be formed by DMLS, which, as described above, is a form of 3-D printing technology. In DMLS, the orthopaedic surgical instrument is formed in a layer-by-layer fashion using laser sintering in which light fuses metallic powder, forming the metallic structures that define the orthopaedic surgical instrument. As part of the process of fabricating the orthopaedic surgical instrument, the metallic powder may be fused in layers, resulting in an orthopaedic surgical instrument that is a single monolithic component that includes a plurality of fused laminations 184. For example, as shown in FIG. 8, the cutting block 10 includes a plurality of fused laminations 184 of metallic material of uniform thickness. It should be appreciated that other forms of 3-D printing technology such as, for example, optical fabrication, photo-solidification, or resin printing may be used to fabricate the orthopaedic surgical instrument.

As described above, the cutting block 10 includes a pair of guide bosses 140 that have tapered anterior surfaces 152. In one exemplary process, the cutting block 10 may be fabricated with the anterior elongated opening 110 cutting slot 12 pointing downward. By tapering the anterior surfaces 152, no support structure is needed to keep the bosses 140 from collapsing during fabrication. It should be appreciated that other surfaces that face downward during the build may be tapered/angled to minimize the amount of support structure needed. In the illustrative embodiment, the tapered surfaces 152 are angled by about 35 degrees. As used herein, the term "about" should be understood to refer to permit the normal tolerances created by manufacturing variation and other design criteria.

After the customized patient-specific orthopaedic surgical instrument is fabricated, the surgeon may perform the orthopaedic surgical procedure using the customized patient-specific orthopaedic surgical instrument. As discussed above, because the orthopaedic surgeon does not need to determine the proper location of the orthopaedic surgical instrument intra-operatively, which typically requires some amount of estimation on part of the surgeon, the guesswork and/or intra-operative decision-making on part of the orthopaedic surgeon is reduced.

It should also be appreciated that variations in the bony of anatomy of the patient may require more than one customized patient-specific orthopaedic surgical instrument to be fabricated according to the method described herein. For example, the patient may require the implantation of two orthopaedic prostheses. As such, the surgeon may follow the method 200 of FIGS. 11A-B to fabricate a different customized patient-specific orthopaedic surgical instrument for use in replacing each portion of the patient's bony anatomy. Each customized patient-specific orthopaedic surgical instrument defines a cutting plane or other relevant parameter relative to each bone that is different due to the variation in the bony anatomy.

One such instrument—a customized patient-specific tibial cutting block 310—is shown in FIGS. 16-22. The tibial cutting block 310 includes a cutting guide slot 312 position to guide a customized, patient-specific resection of a proximal end of a patient's tibia along a predetermined resection plane. As described in greater detail below, the tibial cutting block 310 is configured to be coupled to a patient's tibia in a unique pre-determined location and orientation. It illustrative embodiment, the structure of the cutting block 310, like the structure of the femoral cutting block 10 described above, has been contoured to reduce its size relative to conventional cutting blocks and avoid contact with undesirable regions of the patient's bone.

Figure 16:
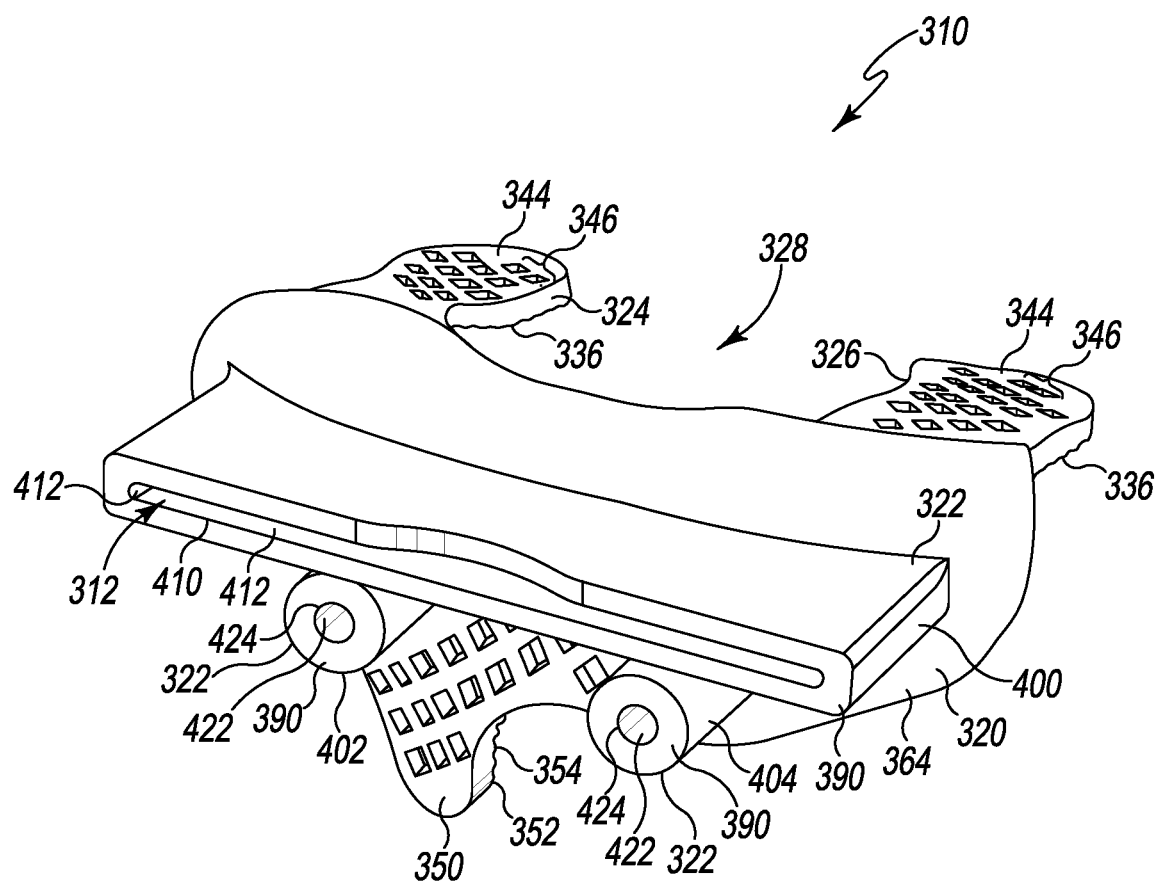
FIG. 16 is a perspective view of a customized patient-specific orthopaedic tibial cutting block.

As shown in FIG. 16, the tibial cutting block 310 includes a base plate 320 and a number of surgical tool guide bodies 322 that are attached to, and extend outwardly from, the base plate 320. Like the femoral cutting block 10, the tibial cutting block 310 is a single monolithic component formed via a 3-D printing process from a metallic material such as, for example, stainless steel. In the illustrative embodiment, the base plate 320 includes a pair of arms 324, 326 that are configured to engage a proximal end of the patient's tibia. The arms 324, 326 are spaced apart from each other such that a notch 328 is defined between their respective inner edges. The notch 328 is sized and shaped to receive the natural spine of the patient's tibia. In that way, base plate 320 is shaped to engage the medial and lateral tibial compartments of the patient's natural tibia in avoid contact with the spine.

Figure 19:
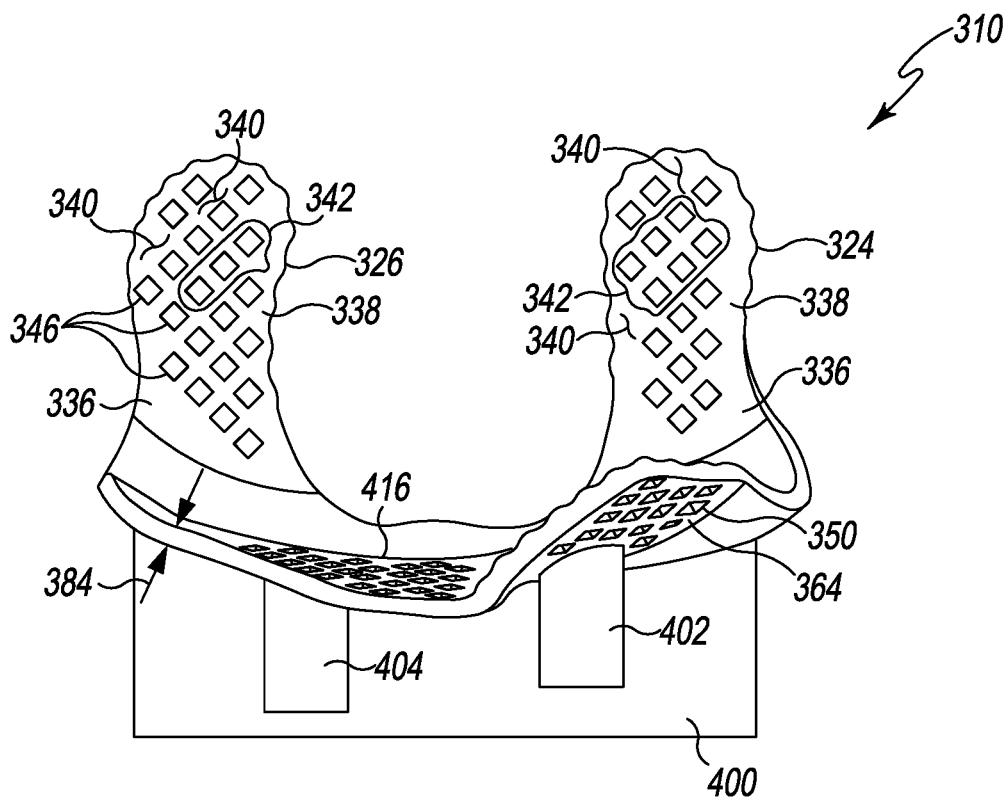
FIG. 19 is a distal plan view of the cutting block of FIG. 16.
Figure 20:
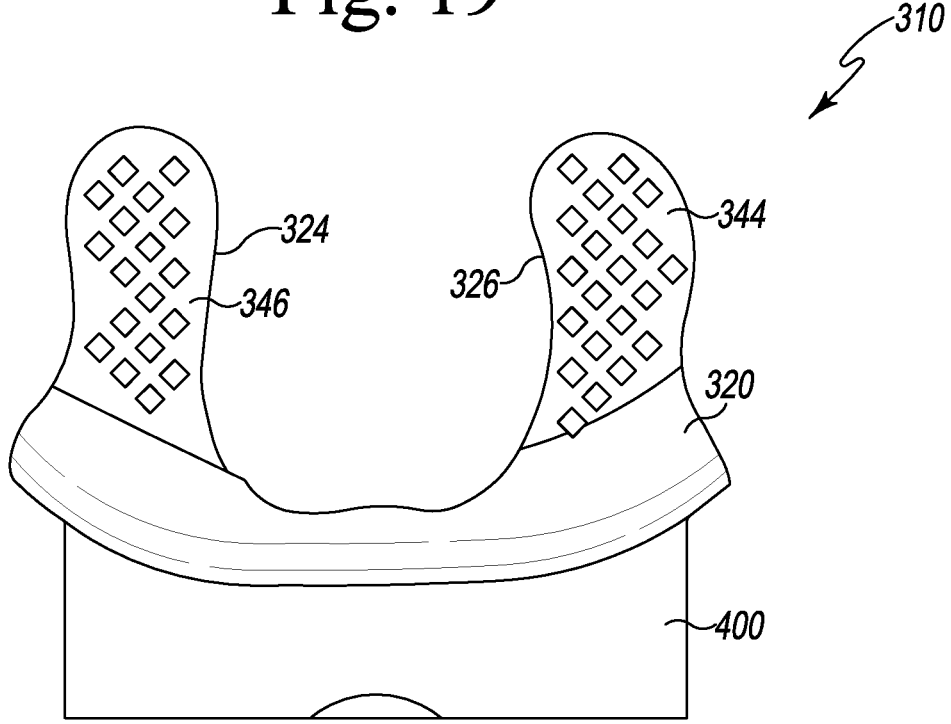
FIG. 20 is a proximal plan view of the cutting block of FIG. 16.
Figure 21:
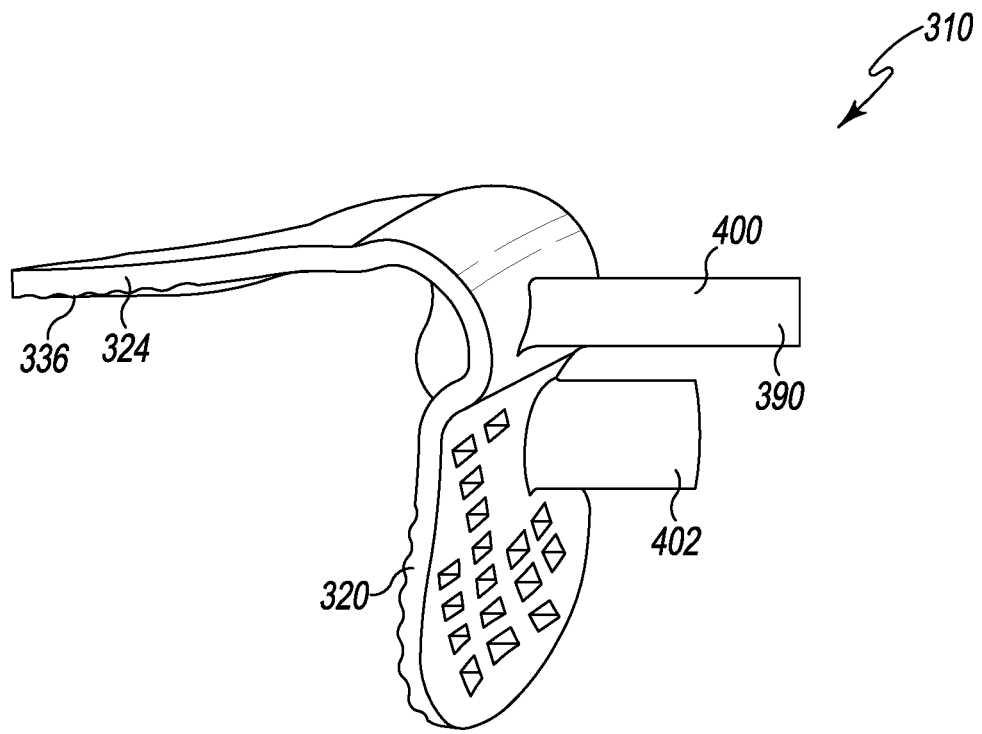
FIG. 21 is a side elevation view of the cutting block of FIG. 16.
Figure 22:
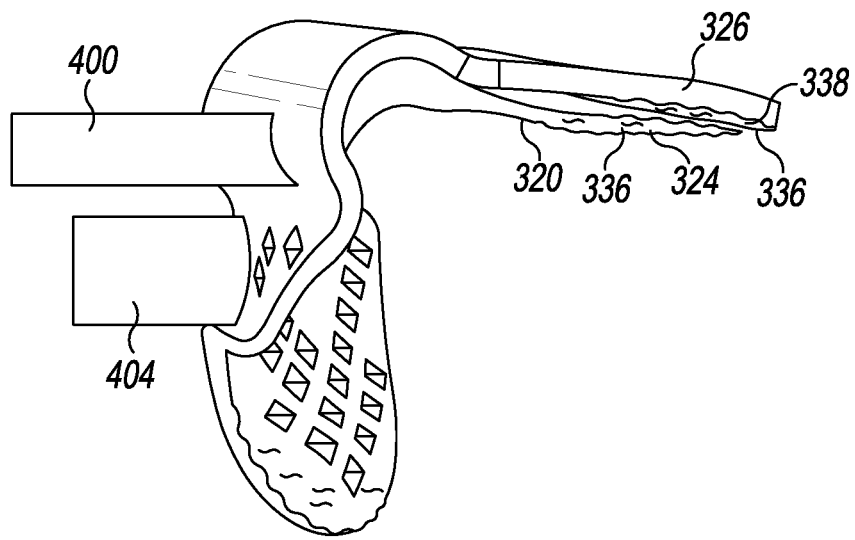
FIG. 22 is another side elevation view of the cutting block of FIG. 16.
Figure 23:
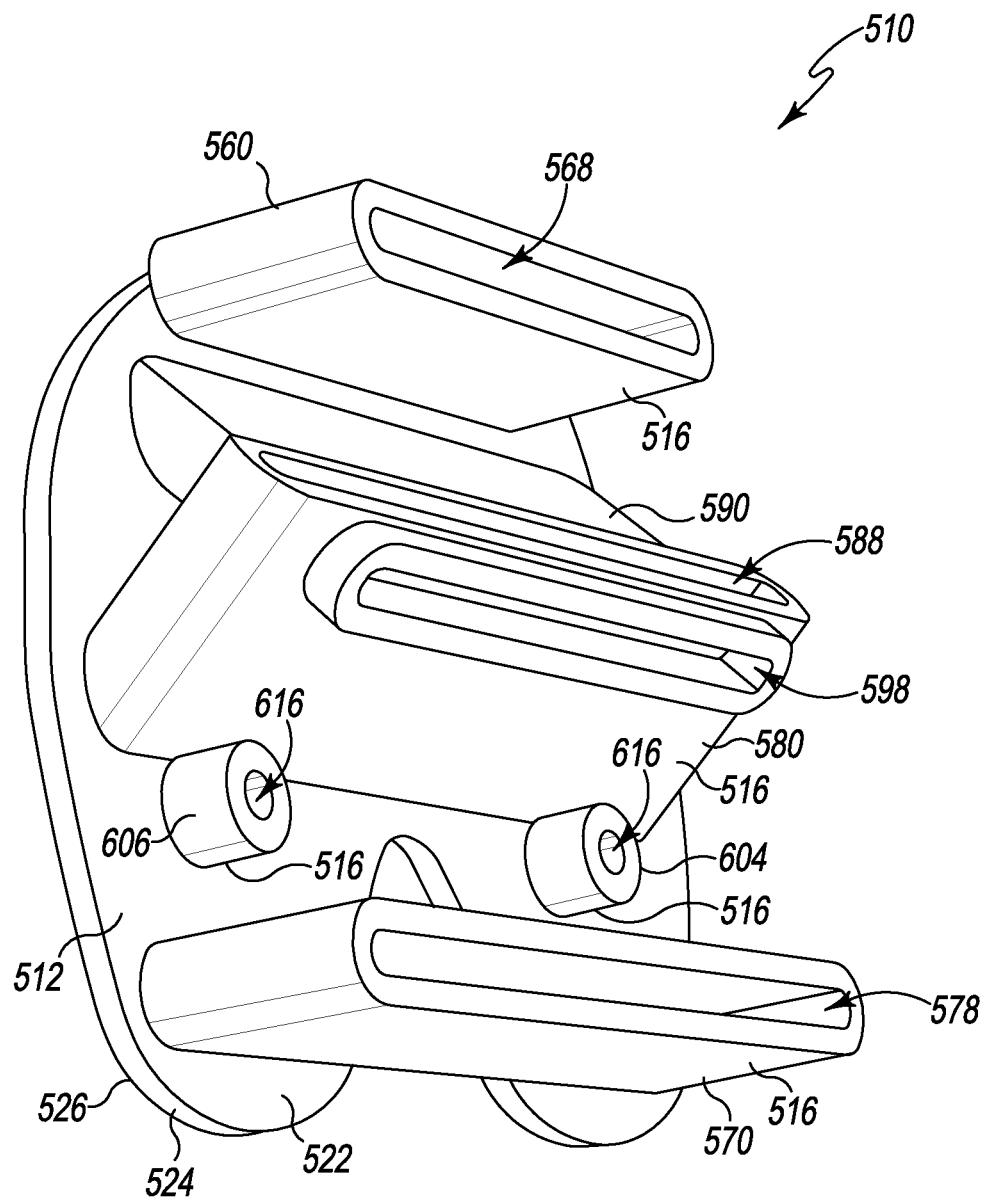
FIG. 23 is a perspective view of a customized patient-specific orthopaedic femoral cutting guide.

Each of the arms 324, 326 includes a bone-facing surface 336 that engages the medial or lateral tibial compartment. As shown in FIG. 19, each bone-facing surface 336 includes a negative contour 338 that is configured to receive a portion of the patient's tibia. Each contour 338 includes a unique set of ridges 340 and depressions 342 that are shaped to engage a corresponding set of depressions and ridges of the patient's tibia. Each of the arms 324, 326 also includes an outer surface 344 that is positioned opposite the corresponding bone-facing surface 336. In the illustrative embodiment, a plurality of apertures 346 extend through the surfaces 336, 344. Each aperture 346 is illustratively diamond-shaped and includes edges that are configured to grip the bone.

Figure 17:
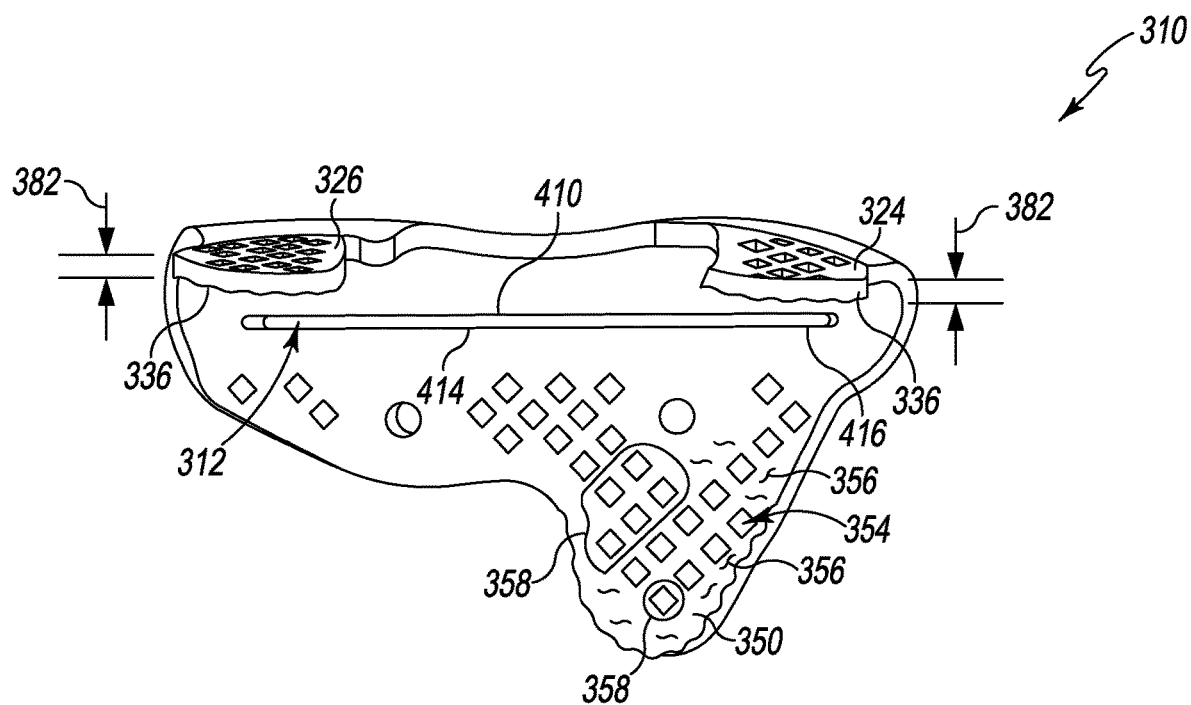
FIG. 17 is a posterior side elevation view of the cutting block of FIG. 16.
Figure 18:
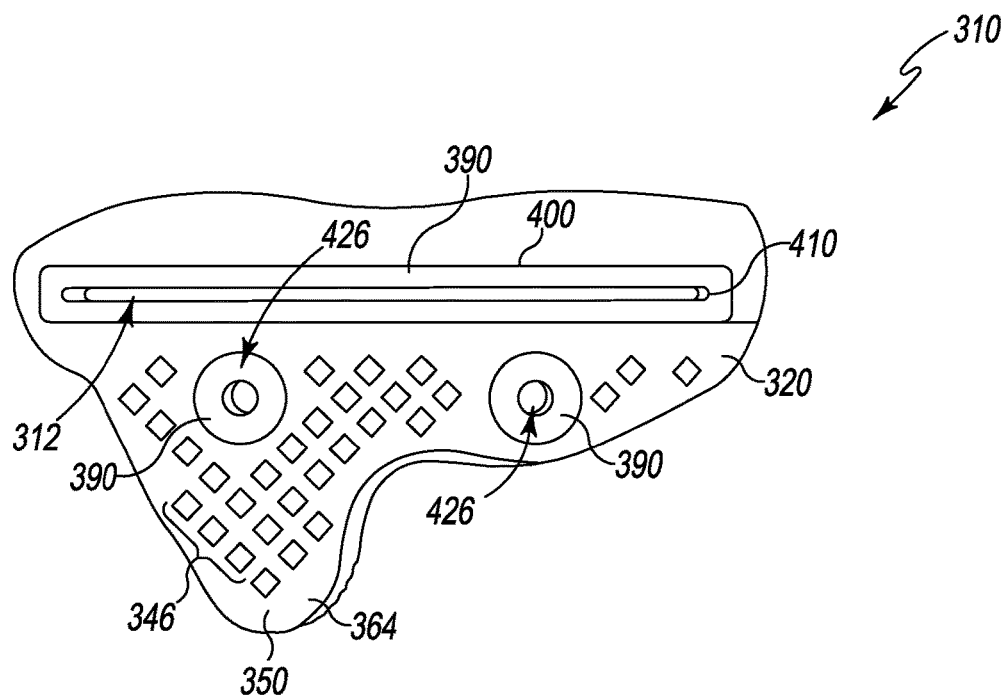
FIG. 18 is an anterior side elevation view of the cutting block of FIG. 16.

The base plate 320 also includes an anterior flange 350 that is configured to engage the proximal end of the patient's tibia. As shown in FIG. 17, the anterior flange 350 includes a bone-facing surface 352, and a negative contour 354 is defined in the bone-facing surface 352. The negative contour 354 is configured to receive a portion of the patient's tibia in includes a unique set of ridges 356 and depressions 358 that are shaped to engage a corresponding set of depressions and ridges of the patient's tibia. The anterior flange 350 also includes an outer surface 364 that is positioned opposite the bone-facing surface 352. In the illustrative embodiment, a plurality of apertures 346 also extend through the surfaces 352, 364. Each aperture 346 is illustratively diamond-shaped and includes edges that are configured to grip the bone. It should be appreciated that in other embodiments the apertures may have different geometric shapes or may be omitted. Similarly, it should be appreciated that the femoral cutting block 10 described above may, in other embodiments, include such apertures.

In the illustrative embodiment, the notch 328 defined between the arms 324, 326 is a customized cavity similar to the customized cavity 70 described above in regard to the femoral cutting block 10. It should also be appreciated that in other embodiments the base plate 320 may include additional customized cavities similar to the customized cavities 70. Such cavities may be sized and shaped to be positioned over problematic regions of the patient's tibia in the pre-determined location of the bone such that those regions may be avoided so as to not interfere with the positioning of the cutting block 310.

In the illustrative embodiment, the base plate 320 of the cutting block 310 also has a low-profile to reduce the size of the incision and reduce the amount of bone displacement needed to position the cutting block 310. The low-profile has been customized for block 310 by minimizing the thicknesses of the arms 324, 326 and the anterior flange 350. As shown in FIG. 17, a thickness 382 is defined between the outer surface 348 and the bone-facing surface 336 of each arm. The outer surfaces 348 are shaped to follow the geometries of the bone-facing surfaces 336 of the arms 324, 326. Similarly, as shown in FIG. 19, a thickness 384 is defined between the outer surface 364 and the bone-facing surface 352 of the anterior flange 350, and the outer surface 364 of the flange 350 is shaped to follow the geometry of the bone-facing surface 352 to minimize the thickness 384.

As shown in FIGS. 16-22, each of the surgical tool guide bodies 322 of the cutting block 310 is attached to and extends outwardly from the outer surfaces 348, 364 of the arms 324, 326 and the anterior flange 350 to a free end 390 that is spaced apart from the base plate 320. In the illustrative embodiment, the guide bodies 322 include an elongated body 400 and a pair of bosses 402, 404 that extend outwardly from the anterior flange 350. The elongated body 400 includes an elongated opening 410 that is defined in its free end 390, and a number of inner walls 412 extend inwardly from the opening 410. As shown in FIG. 17, the inner walls 412 extend to another opening 414 that is defined by an edge 416 of the bone-facing surface 352. The edge 416 illustratively follows a curved path to match the shape of the patient's tibia in that region. The opening 414 cooperates with the inner walls 412 and the elongated opening 410 to define the guide slot 312, which is sized and shaped to guide a surgical tool such as, for example, a cutting blade, into engagement with the patient's bone. As described above, the cutting guide slot 312 is positioned to guide a customized, patient-specific resection of the proximal end of a patient's tibia. Because the edge 416 follows the shape of the patient's tibia, the cutting guide slot 312 provides support for the cutting blade in close proximity to the region under resection.

As shown in FIG. 16, each of the bosses 402, 404 are positioned distal of the elongated body 400. An opening 420 is defined in the free end 390 of each of the bosses 402, 404, and an inner wall 422 extends inwardly from the opening 420. As shown in FIG. 17, each inner wall 422 extends to another opening 424 in the bone-facing surface 352 to define a guide slot 426 extending through the cutting block 310. In the illustrative embodiment, each guide slot 426 is a drill guide and fixation pin guide hole, which is sized and shaped to guide a surgical drill to prepare the patient's bone to receive a fixation pin to couple to the block 310 to the bone.

Figure 27:
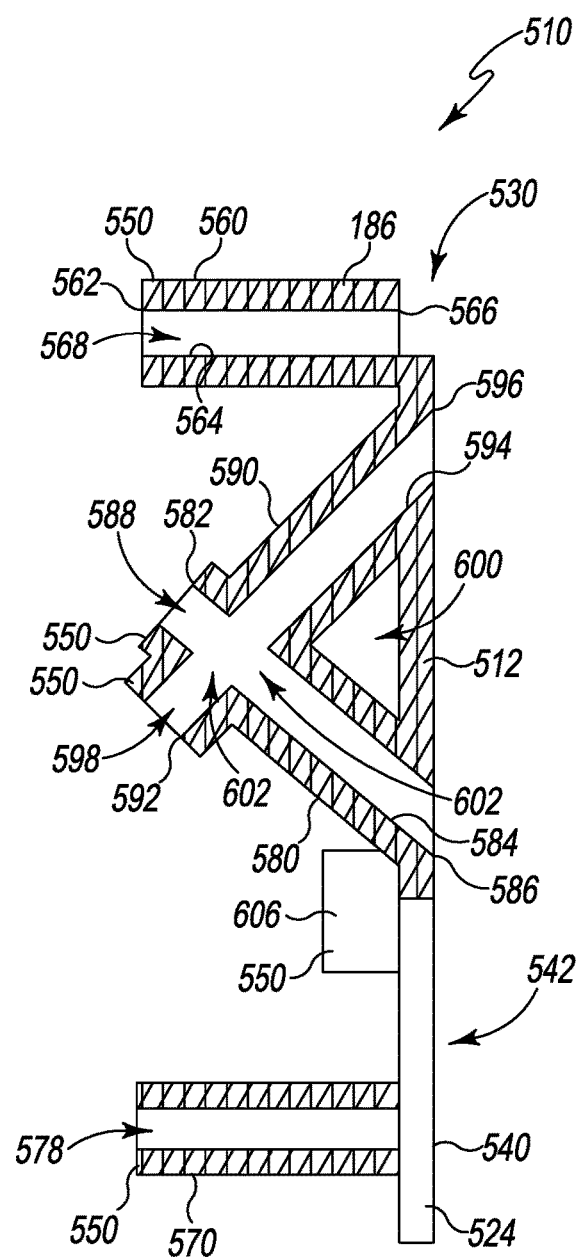
FIG. 27 is a cross-sectional elevation view taken along the line 27-27 and FIG. 24.

Another customized patient-specific orthopaedic surgical instrument that may be modeled and fabricated using the routine 200 is the customized patient-specific anterior-posterior chamfer cutting block 510 shown in FIGS. 23-30. The cutting block 510 includes a base plate 512 that has been customized to fit a distal end 514 of a patient's femur 16 that has been resected using, for example, the femoral cutting block 10 described above. The cutting block 510 also includes a plurality of surgical tool guide bodies 516, which are attached to an extend outwardly from the base plate 512 and which are configured to guide surgical tools into contact with the patient's femur, as described in greater detail below. In the illustrative embodiment, the cutting block 510 is a single monolithic component form from a metallic material such as, for example, stainless steel. In that way, the base plate 512 and the guide bodies 516 form a single monolithic metallic block. Like the cutting blocks 10, 310, the cutting block 510 is formed by DMLS. As shown in FIG. 27, the cutting block 510 includes a plurality of fused laminations 184 of metallic material of uniform thickness.

Figure 25:
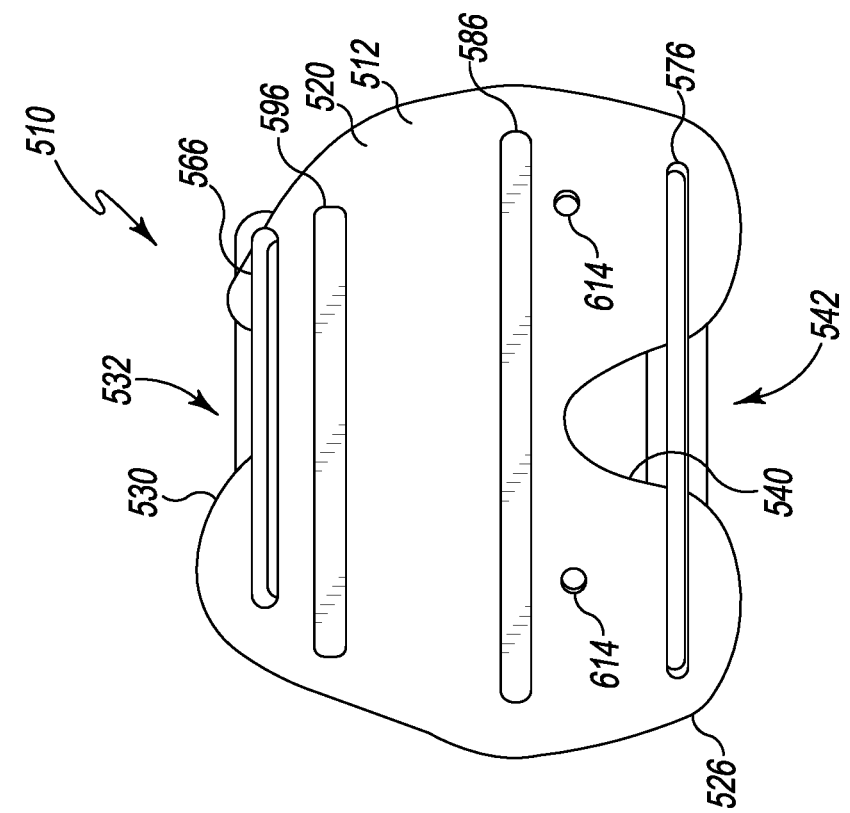
FIG. 25 is a proximal plan view of the femoral cutting guide of FIG. 23.
Figure 24:
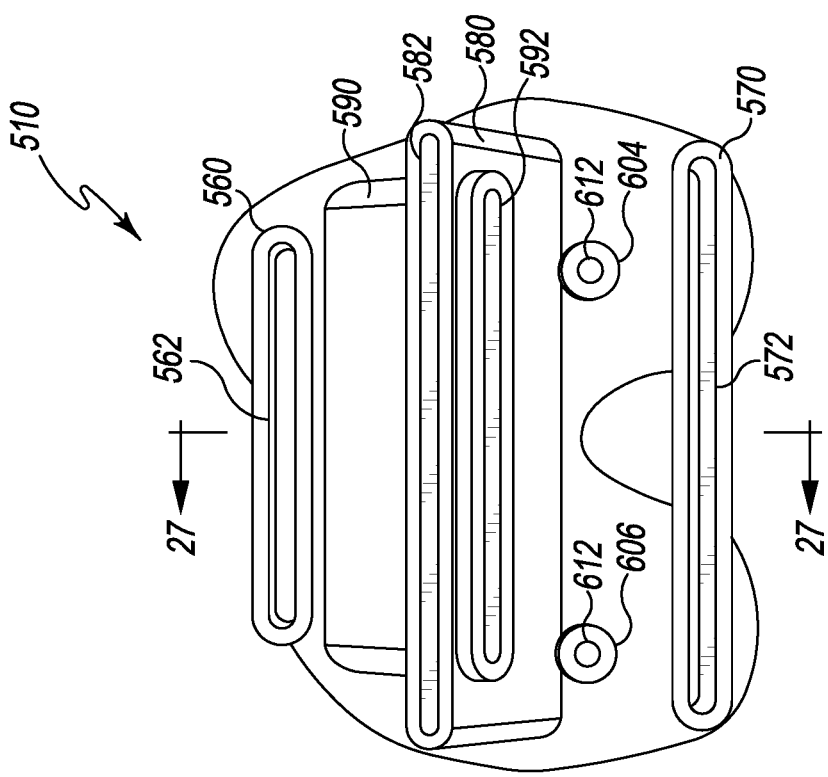
FIG. 24 is a distal plan view of the femoral cutting guide of FIG. 23.
Figure 26:
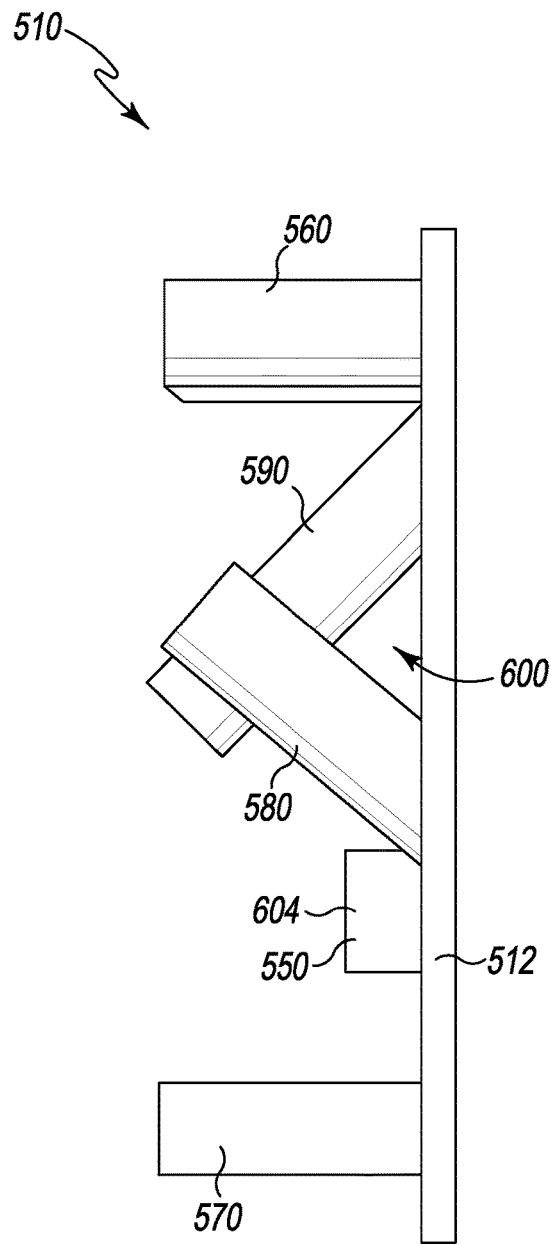
FIG. 26 is a side elevation view of the femoral cutting guide of FIG. 23.

The base plate 512 includes a bone-facing surface 520 and an outer surface 522 that is positioned opposite the bone-facing surface 520. An outer wall 524 extends between the surfaces 520, 522 to define the outer perimeter of the base plate 512. As shown in FIG. 25, the bone-facing surface 520 includes an outer edge 526 that is connected to the outer wall 524 and has been customized to match an outer edge 528 (see FIG. 28) of the resected distal end 514 of a patient's femur 16. In that way, the cutting block 510 is configured to be coupled to the patient's femur 16 in a unique pre-determined location and orientation.

The outer edge 526 includes a superior section 530 that defines a notch 532 in the base plate 512. In the illustrative embodiment, the superior section 530 is curved to match the curvature of the anterior edge section 534 (see FIG. 28) of the resected distal end 514 of a patient's femur 16. The outer edge 526 of the bone-facing surface 520 also includes an inferior section 540 that defines a notch 542 in the base plate 512. In the illustrative embodiment, the inferior section 540 is curved to match the curvature of the posterior edge section 544 (see FIG. 28) of the resected distal end 514 of a patient's femur 16, and the shape of the notch 532 substantially matches the shape of the edge of the intercondylar notch 30.

In the illustrative embodiment, the base plate 512 of the cutting block 510 has a low-profile to reduce the size of the incision and reduce the amount of bone displacement needed to position the cutting block 510. Similar to the blocks 10, 310, the low-profile has been customized for block 510 by minimizing the thickness of the base plate 512 defined between the outer surface 522 and the bone-facing surface 520.

As shown in FIGS. 22-27, each of the surgical tool guide bodies 516 of the cutting block 510 is attached to and extends outwardly from the outer surface 522 to an outer end 550 that is spaced apart from the base plate 512. In the illustrative embodiment, the guide bodies 516 include an anterior resection guide body 560 that is positioned over the notch 532 of the base plate 512. The resection guide body 560 includes an elongated opening 562 that is defined in its outer end 550, which is a free end spaced apart from the outer ends of the other guide bodies 516. The resection guide body 560 also includes a number of inner walls 564 that extend inwardly from the opening 562. As shown in FIG. 25, the inner walls 564 extend to an opening 566 that opens into the superior notch 532 of the base plate 512. The opening 566 cooperates with the inner walls 564 and the elongated opening 562 to define the guide slot 568, which is sized and shaped to guide a surgical tool such as, for example, a cutting blade, into engagement with the patient's femur and guide the anterior resection of the femur along a predetermined resection plane. The cutting guide slot 568 is positioned in a unique, predetermined position and orientation that has been customized for that patient.

The guide bodies 516 include a posterior resection guide body 570 that is positioned over the inferior notch 542 of the base plate 512. The resection guide body 570 includes an elongated opening 572 that is defined in its outer end 550, which is a free end spaced apart from the outer ends of the other guide bodies 516. The resection guide body 570 also includes a number of inner walls 574 that extend inwardly from the opening 572. As shown in FIG. 25, the inner walls 574 extend to an opening 576 that opens into the inferior notch 542 of the base plate 512. The opening 576 cooperates with the inner walls 574 and the elongated opening 572 to define the guide slot 578, which is sized and shaped to guide a surgical tool such as, for example, a cutting blade, into engagement with the patient's femur and guide the posterior resection of the femur along a predetermined resection plane. The cutting guide slot 568 is positioned in a unique, predetermined position and orientation that has been customized for that patient.

The guide bodies 516 also include a pair of chamfer resection guide bodies 580, 590 that are positioned between the anterior and posterior resection guide bodies 560, 570. The resection guide body 580 includes an elongated opening 582 that is defined in its outer end 550, and a number of inner walls 584 that extend inwardly from the opening 582. As shown in FIG. 25, the inner walls 584 extend to an opening 586 defined in the bone-facing surface 520 of the base plate 512. The opening 586 cooperates with the inner walls 584 and the elongated opening 582 to define a chamfer resection guide slot 588, which is sized and shaped to guide a surgical tool such as, for example, a cutting blade, into engagement with the patient's femur and guide a chamfer resection of the femur along a predetermined resection plane, which extends at an angle relative to the resection planes defined by the other cutting guide slots. The cutting guide slot 588 is positioned in a unique, predetermined position and orientation that has been customized for that patient.

The resection guide body 590 includes an elongated opening 592 that is defined in its outer end 550, and a number of inner walls 594 that extend inwardly from the opening 592. As shown in FIG. 25, the inner walls 594 extend to an opening 596 defined in the bone-facing surface 520 of the base plate 512. The opening 596 cooperates with the inner walls 594 and the elongated opening 592 to define another chamfer guide slot 598, which is sized and shaped to guide a surgical tool such as, for example, a cutting blade, into engagement with the patient's femur and guide another chamfer resection of the femur along a predetermined resection plane, which also extends at an angle relative to the resection planes defined by the other cutting guide slots. The cutting guide slot 598 is positioned in a unique, predetermined position and orientation that has been customized for that patient.

As shown in FIGS. 22-27, the outer ends 550 of the chamfer resection guide bodies 580, 590 are coupled together, and a passageway 600 is defined between the surfaces of the guide bodies 580, 590 and the base plate 512. In the illustrative embodiment, the passageway 600 has a triangular cross-section. As shown in FIG. 27, the guide slots 588, 598 of the guide bodies 580, 590 intersect, and the inner walls 584, 594 of the guide bodies 580, 590 include a number of openings 602 at the intersection such that the guide slots 588, 598 are in communication with each other.

The guide bodies 516 also include a pair of bosses 604, 606 that extend outwardly from the base plate 512 between the chamfer resection guide bodies 580, 590 and the posterior resection guide body 570. An opening 610 is defined in the outer end 550 of each of the bosses 604, 606, and an inner wall 612 extends inwardly from the opening 610. As shown in FIG. 17, each inner wall 612 extends to another opening 614 in the bone-facing surface 520 to define a guide slot 616 extending through the cutting block 510. In the illustrative embodiment, each guide slot 616 is a drill guide and fixation pin guide hole, which is sized and shaped to guide a surgical drill to prepare the patient's bone to receive a fixation pin to couple to the block 510 to the patient's femur.

Figure 28:
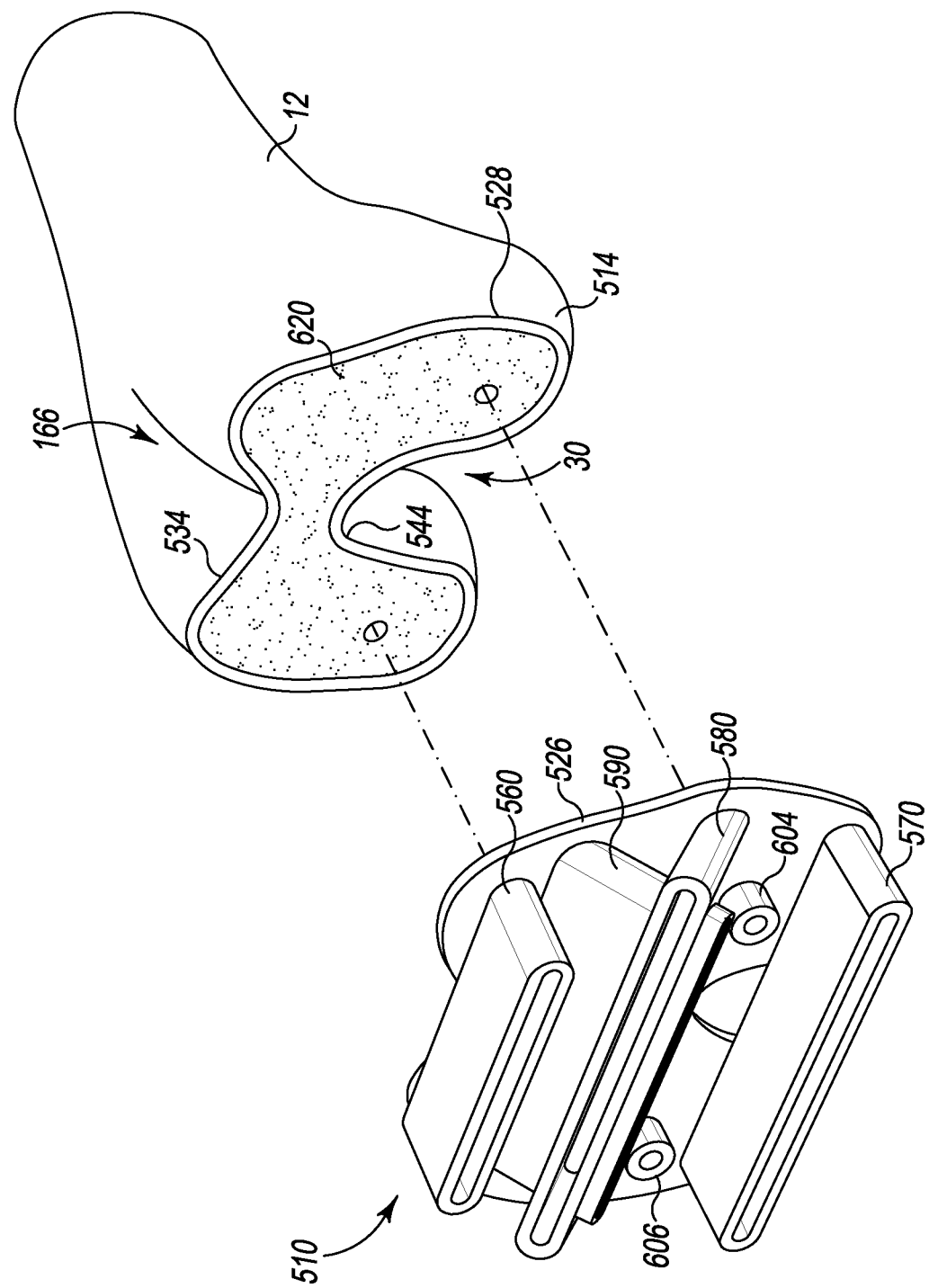
FIG. 28 is a perspective view of the femoral cutting guide of FIG. 23 aligned with a resected distal end of the patient's femur.

As described above, the cutting block A-P chamfer cutting block 510 is customized to fit a resected distal end 514 of a patient's femur 16, which is shown in FIG. 28. The resected distal end 514 includes a resected distal surface 620 that is bounded by the outer edge 528. As shown in FIG. 28, the outer edge 528 includes an anterior edge section 534 that defines the distal opening of the patient's trochlear groove 166 and a posterior edge section 544 that defines the distal opening of the patient's intercondylar notch 30. In the illustrative embodiment, the size and shape of the resected distal surface 620 is pre-operatively planned during, for example, the execution of the routine 200. In other words, when the surgeon or other user defines the distal resection plane to be created using the cutting block 10, the size and shape of the resected distal surface 620 is also modeled. With the model of the resected distal surface 620, the user may generate a 3-D computer model of the A-P chamfer cutting guide block 510 during the process step 226 of the routine 200.

Figure 29:
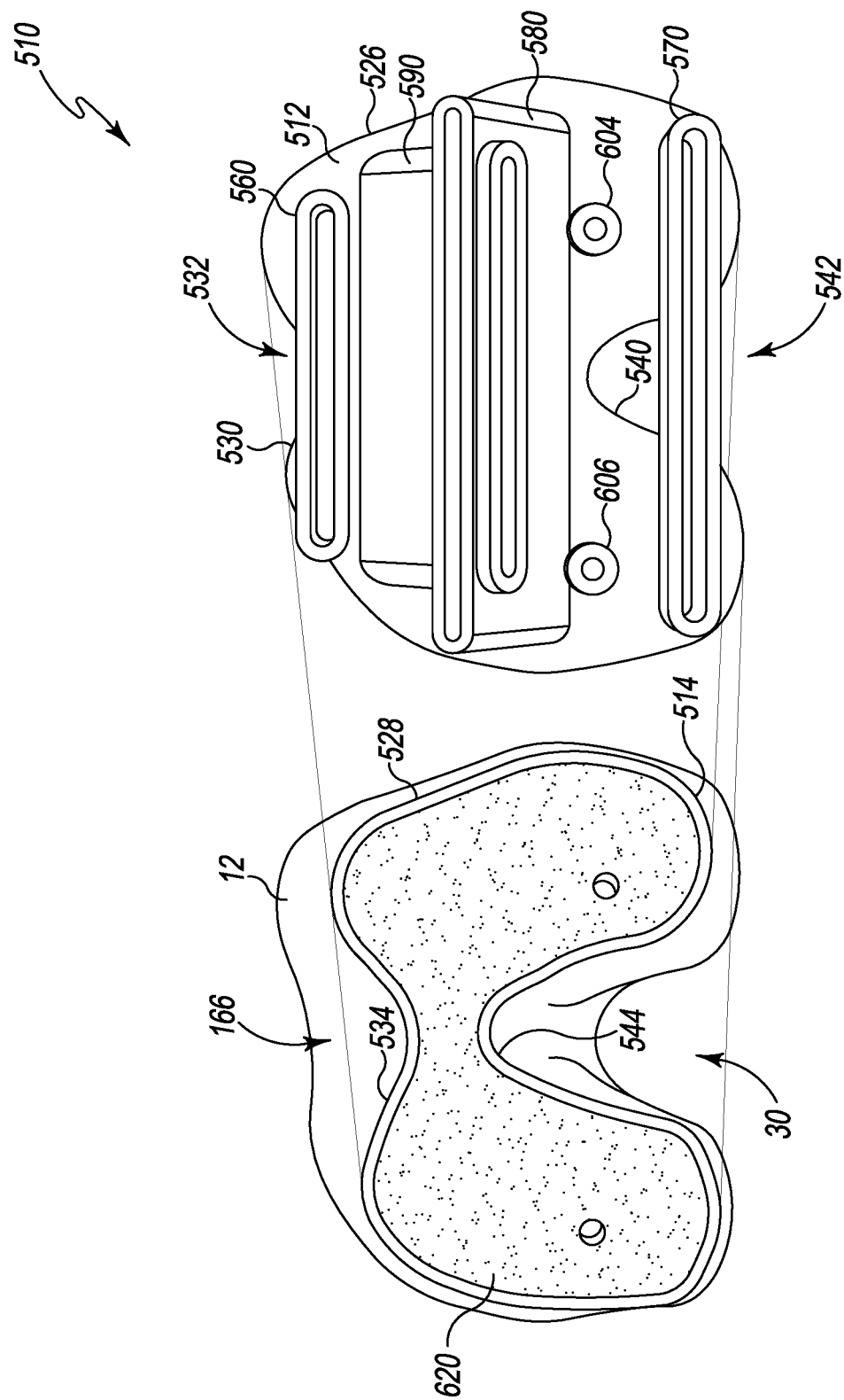
FIG. 29 is an elevation view showing that the femoral cutting guide of FIG. 23 is sized and shaped to match the resected distal end of the patient's femur.
Figure 30:
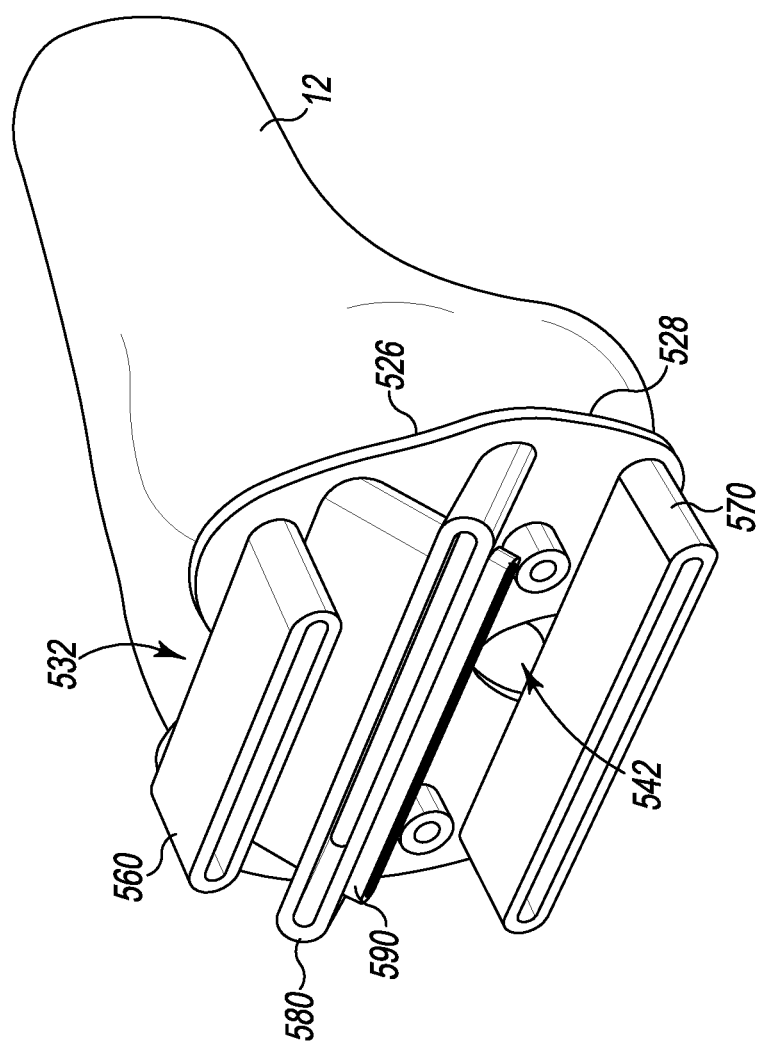
FIG. 30 is a perspective view of the femoral cutting guide of FIG. 23 positioned on the resected distal end of the patient's femur.

As shown in FIG. 29 and described above, the outer edge 526 of the base plate 512 of the cutting block 510 is shaped to match the outer edge 528 of the resected distal surface 620. In particular, the superior section 530 of the plate outer edge 526 is curved to match the curvature of the anterior edge section 534 of the outer edge 528 of the resected distal surface 620, and the inferior section 540 of the plate outer edge 526 is curved to match the curvature of the posterior edge section 544 of the outer edge 528 of the resected distal surface 620. The superior notch 532 of the base plate 512 is shaped to match the distal opening of the patient's trochlear groove 166. The base plate 512 also includes the inferior notch 542 that is shaped to match the distal opening of the patient's intercondylar notch 30. As shown in FIG. 30, the outer edges 526, 528 of the block and bone are coincident when the cutting block 510 is properly positioned on the patient's bone, with the notches 532, 542 aligned with the distal openings of the groove 166 and the notch 30. In that way, the surgeon or other user are informed when the block is properly positioned and any misalignment with the patient's bone can be corrected prior to beginning any resection with the block 510.

Referring now to FIGS. 31-37, another embodiment of a customized patient-specific femoral cutting block (hereinafter the cutting block 710) is shown. The embodiment of FIGS. 31-37 includes many features that are the same or similar to features shown in the embodiment of FIGS. 1-10. Similar features will be identified in FIGS. 31-37 with the same reference numbers as were used in FIGS. 1-10. The cutting block 710 includes a cutting guide slot 712 positioned to guide a customized, patient-specific resection of a distal end of a patient's femur. As described in greater detail below, the femoral cutting block 710 is configured to be coupled to the patient's femur in a unique pre-determined location and orientation. In the illustrative embodiment, the structure of the cutting block 710 has been contoured to reduce its size relative to conventional cutting blocks and avoid contact with undesirable regions of the patient's bone.

Figure 31:
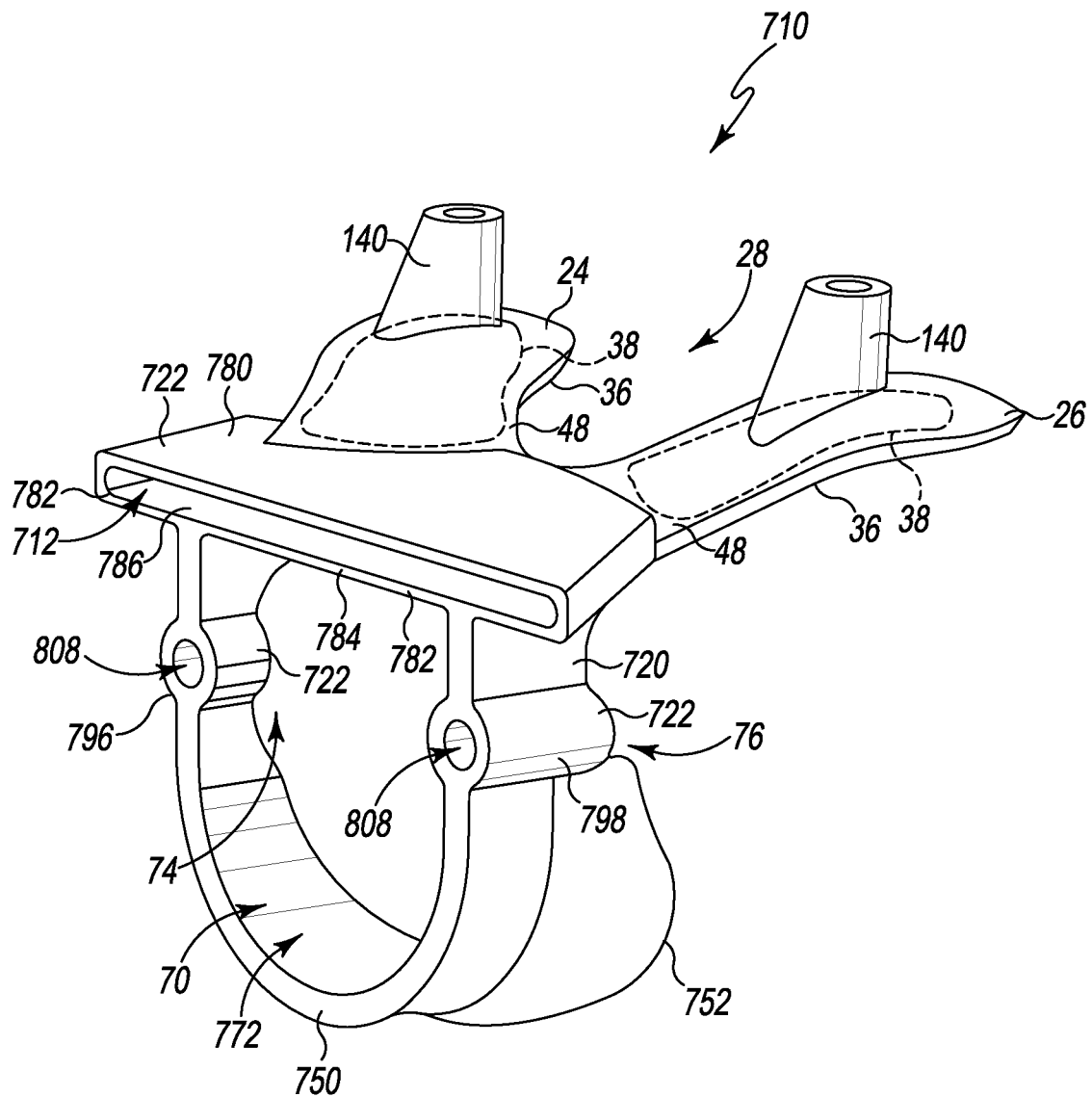
FIGS. 31-37 are views of another embodiment of a customized patient-specific femoral cutting block.

As shown in FIG. 31, the femoral cutting block 710 includes a base plate 720 and a number of surgical tool guide bodies 722 that are attached to, and extend outwardly from, the base plate 720. In the illustrative embodiment, the femoral cutting block 710 is a single monolithic component formed from a metallic material such as, for example, stainless steel, via a DMLS technique. In that way, the base plate 720 and the guide bodies 722 form a single monolithic metallic block.

The base plate 720 includes a posterior section including a pair of arms 24, 26 that are configured to engage the distal end of the patient's femur. The arms 24, 26 are spaced apart from each other such that a notch 28 is defined between the inner edges of the arms 24, 26. The notch 28 is sized and shaped to correspond to the natural intercondylar notch of the patient's femur. In that way, contact within bone surfaces with the natural intercondylar notch 30, which may be difficult to model, is avoided.

Each of the arms 24, 26 has a bone-contacting or bone-facing surface 36 that engages one of the natural condyles 32, 34. In the illustrative embodiment, each bone-facing surface 36 includes a number of negative contours 38 that are configured to receive a portion of the natural condyles 32, 34. Each of the arms 24, 26 also includes an outer surface 48 that is positioned opposite its corresponding bone-facing surface 36. In the illustrative embodiment, each outer surface 48 is substantially smooth.

As shown in FIG. 31, the base plate 720 also includes an anterior section including an anterior flange 750 that is configured to engage the distal end of the patient's femur. In the illustrative embodiment, the flange 750 is spaced apart from the arms 24, 26. The anterior flange 750 includes a bone-facing surface 752 that includes a number of negative contours 754 that are configured to receive a portion of the patient's femur. As shown in, for example, FIGS. 32 and 34, the contour 754 of the anterior flange 750 has a unique set of ridges 756 and depressions 758 that are shaped to engage a corresponding unique set of depressions and ridges of the patient's femur. The anterior flange 750 also includes an outer surface 764 that is positioned opposite the bone-facing surface 752. In the illustrative embodiment, the outer surface 764 is substantially smooth.

Figure 32:
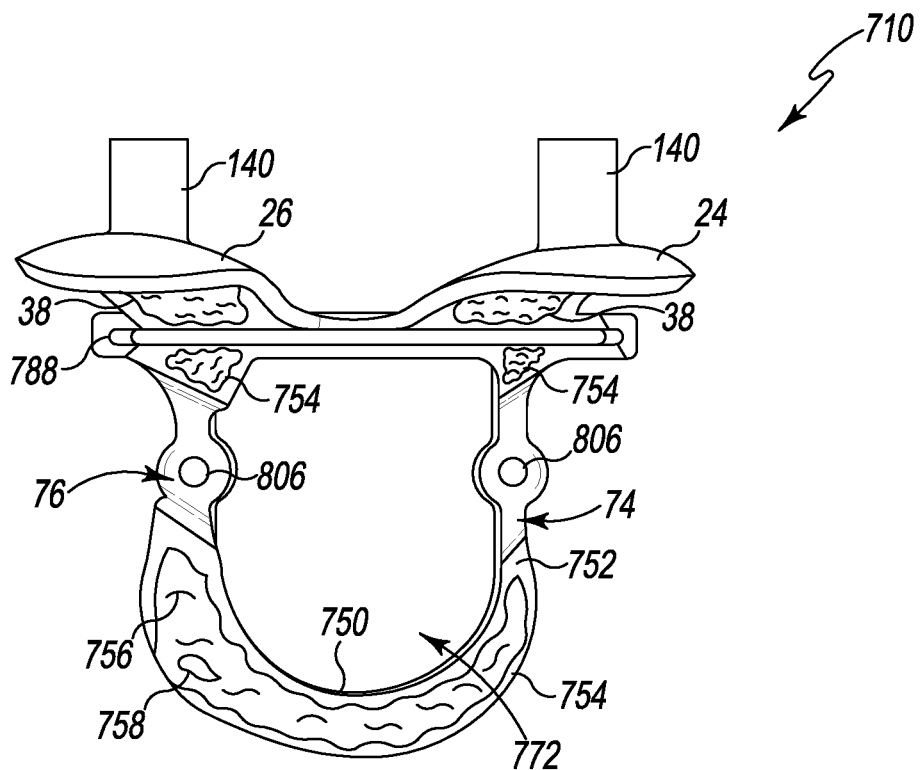
Figure 33:
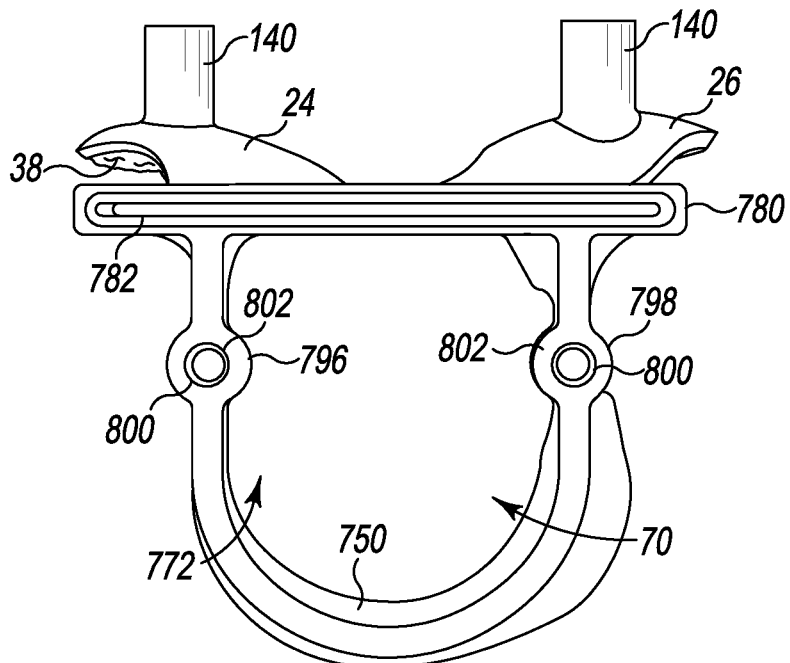
Figure 34:
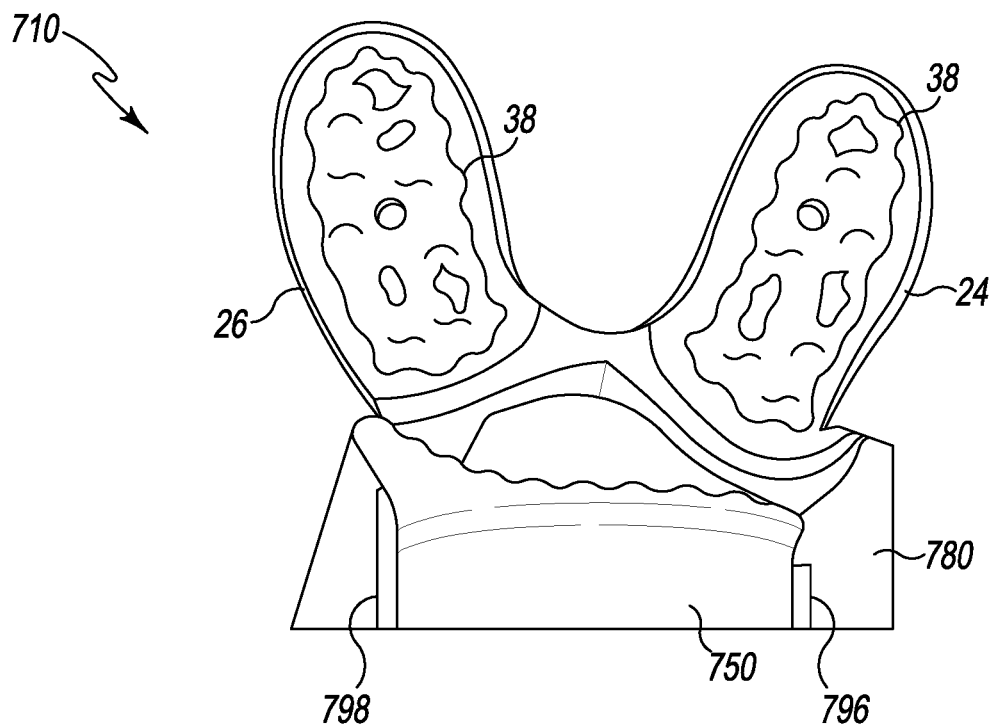

The base plate 720 also includes a number of customized cavities 70, which are sized to be positioned over regions in the pre-determined location of the bone that may include a defect or are damaged or difficult to model. In that way, the cavities 70 are sized such that contact with those regions may be avoided so as to not interfere with positioning the cutting block 10 in the pre-determined location and orientation. In the illustrative embodiment, the notch 28 defined between the arms 24, 26 is one of the customized cavities. As shown in FIGS. 31-33, the customized cavities 70 also include an aperture 772 that extends through the bone-facing surface 752 of the anterior flange 750. As shown in FIGS. 31-32, the customized cavities 70 also include a pair of channels 74, 76 that are defined in the bone-facing surface 752 of the anterior flange 750.

As described above, the cutting block 710 includes a number of surgical tool guide bodies 722 configured to guide a surgical tool into contact with the patient's bone. In the illustrative embodiment, the guide bodies 722 include a distal resection guide body 780 that extends anteriorly from the anterior ends of the arms 24, 26. The distal resection guide body 780 includes an elongated opening 782 that is defined in its outer end 784 and a number of inner walls 786 that extend inwardly from the opening 782. As shown in FIG. 32, the inner walls 786 extend to another opening 788 that is defined in the bone-facing surface 762. The opening 788 cooperates with the inner walls 786 and the elongated opening 782 to define the cutting guide slot 712, which is sized and shaped to guide a surgical tool such as, for example, a cutting blade, into engagement with the patient's bone. As described above, the cutting guide slot 712 is positioned to guide a customized, patient-specific resection of a distal end of a patient's femur.

Figure 35:
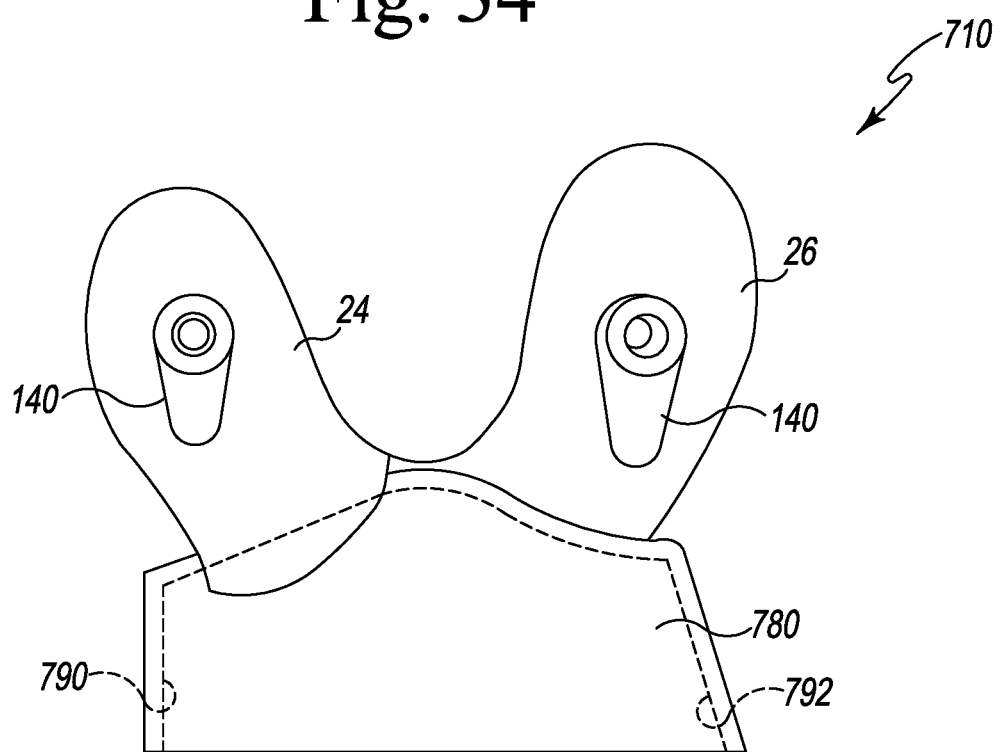

As shown in FIG. 35, the inner walls 786 include a medial inner wall 790 that defines the medial side of the guide slot 712 and a lateral inner wall 792 that defines the lateral side of the guide slot 712. In the illustrative embodiment, the lateral inner wall 792 extends at an oblique angle relative to the medial inner wall 790 to guide the resection of the patient's bone. The oblique angle, like the rest of the cutting guide block 710, is customized to the bony anatomy of the patient. It should be appreciated that the medial inner wall may be angled in other embodiments.

The tool guide bodies 722 of the block 710 also includes a pair of guide bosses 796, 798 that are integrated into the anterior flange 750, which extends proximally from the guide body 780. An opening 800 is defined in the outer surface 802 of each of the bosses 796, 798, and an inner wall 804 extends inwardly from the opening 800. As shown in FIG. 32, each inner wall 804 extends to another opening 806 that opens into one of the channels 74, 76 to define a guide slot 808 extending through the cutting block 710. In the illustrative embodiment, each guide slot 808 is a drill guide and fixation pin guide hole, which is sized and shaped to guide a surgical drill to prepare the patient's bone to receive a fixation pin to couple to the block 710 to the bone.

Figure 36:
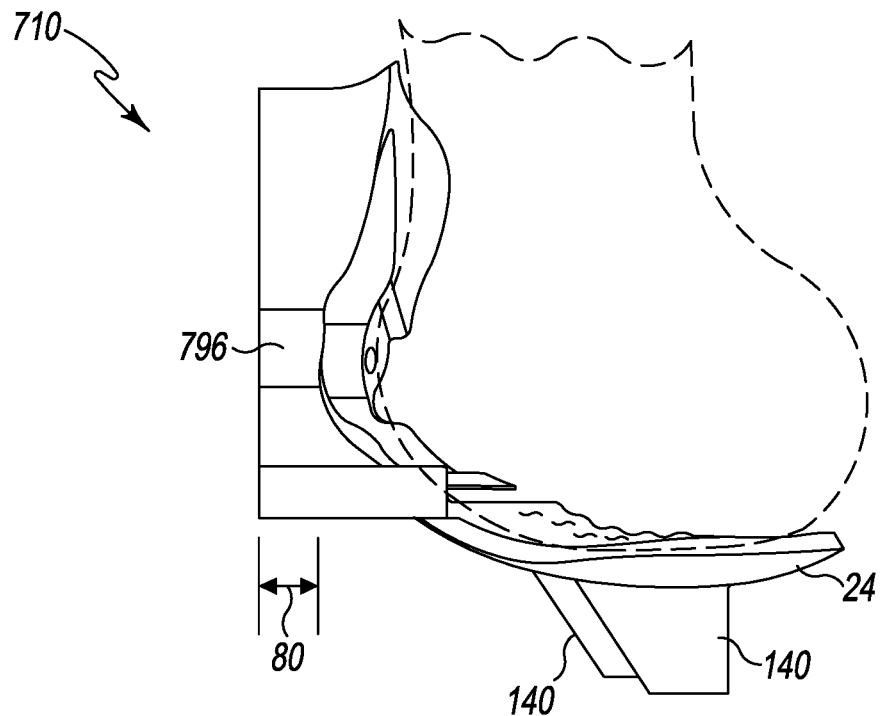
Figure 37:
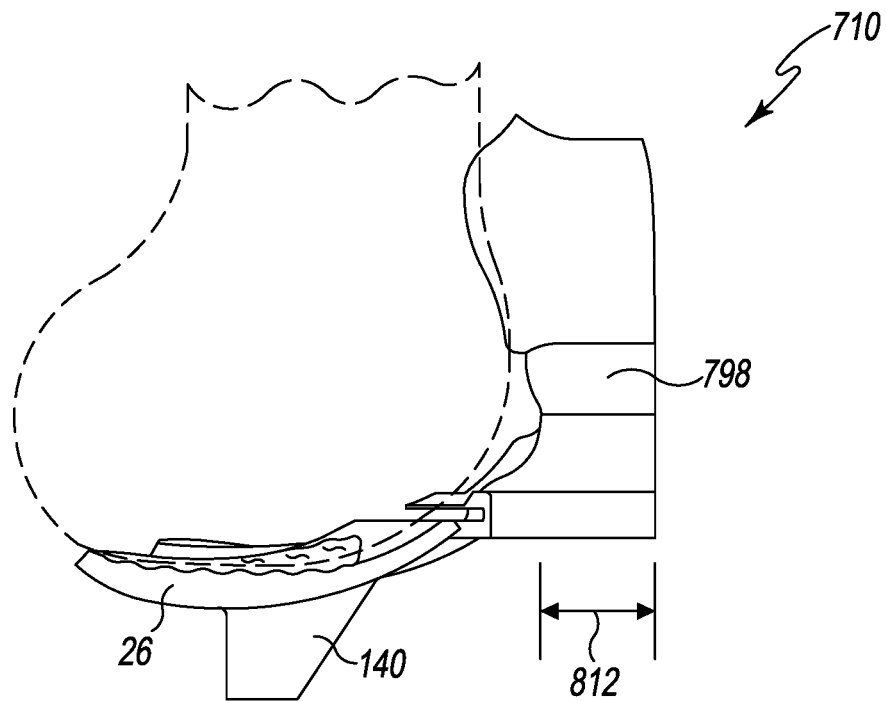

The cutting block 710 has a low-profile to reduce the size of the incision and reduce the amount of bone displacement needed to position the cutting block 710. The low-profile has been customized for block 710 by adjusting the shape and sizes of the base plate and the guide bodies. For example, as shown in FIG. 36, the guide boss 796 has a length 810 that is shorter than the length 812 of the guide boss 798, which is shown in FIG. 36. Similarly, the outer surface 48 of each arm is convexly curved to follow the concave curvature of the bone-facing surface 36 of the arm.

The guide bodies 722 of the cutting block 710 also include a pair of posterior guide bosses 140, which are attached to, and extend distally from, the outer surfaces 48 of the arms 24, 26, respectively. Each posterior guide boss 140 includes a guide slot 142 that is sized and shaped to guide surgical drill and a fixation pin into engagement with the patient's bone to couple to the block 710 to the bone.

Figure 38:
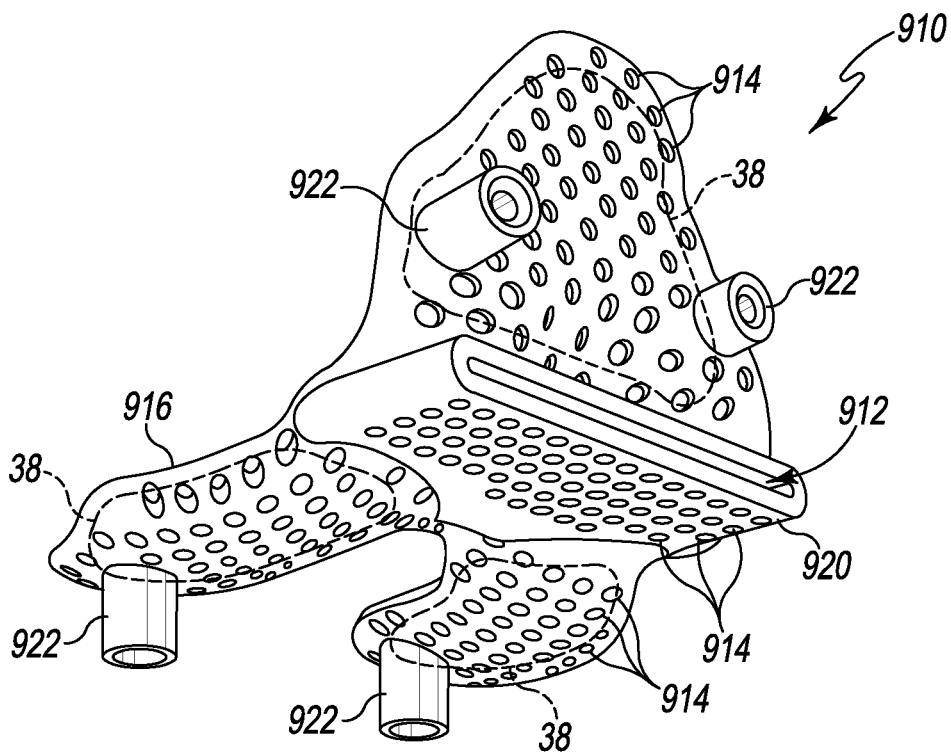
FIG. 38 is a perspective view of another embodiment of a customized patient-specific femoral cutting block.

Referring now to FIGS. 38-41, other embodiments of customized patient-specific cutting blocks (hereinafter the cutting block 910, 1010, 1110) are shown. The embodiments of FIGS. 38-41 include many features that are the same or similar to features shown in the embodiments described above. Similar features will be identified in FIGS. 38-41 with the same reference numbers as were used in reference to the embodiments above. Referring now to FIG. 38, the cutting block 910 includes a cutting guide slot 912 positioned to guide a customized, patient-specific resection of a distal end of a patient's femur. In the illustrative embodiment, the cutting block 910 includes a number of bone-facing surfaces 916 that have negative contours 38 that are configured to receive portions of the patient's bone.

Similar to the tibial cutting block 310, the cutting block 910 includes a plurality of apertures 914 that extend through the bone-facing surfaces 916 and the outer surfaces 918 of the cutting block 910. Each aperture 914 is illustratively cylindrical in shape and includes a circular edge that is configured to grip the bone. The apertures 914 also extend through the surfaces of the anterior resection guide body 920 and open into the guide slot 912. In that way, the apertures 914 provide viewing windows for the surgeon or other user to monitor the movement of the cutting saw blade and review the fit of the block 910 on the bone. It should be appreciated that similar apertures may be incorporated into any of the embodiments described herein. Additionally, it should be appreciated that the apertures may take other sizes and shapes depending on the nature of the patient's bony anatomy.

The cutting block 910 includes a number of other surgical tool guide bodies 920. In the illustrative embodiment, each of the tool guide bodies 920 is a drill guide and fixation guide configured to guide a fixation pin into engagement with a patient's bone to couple the cutting block 910 to the bone.

Figure 39:
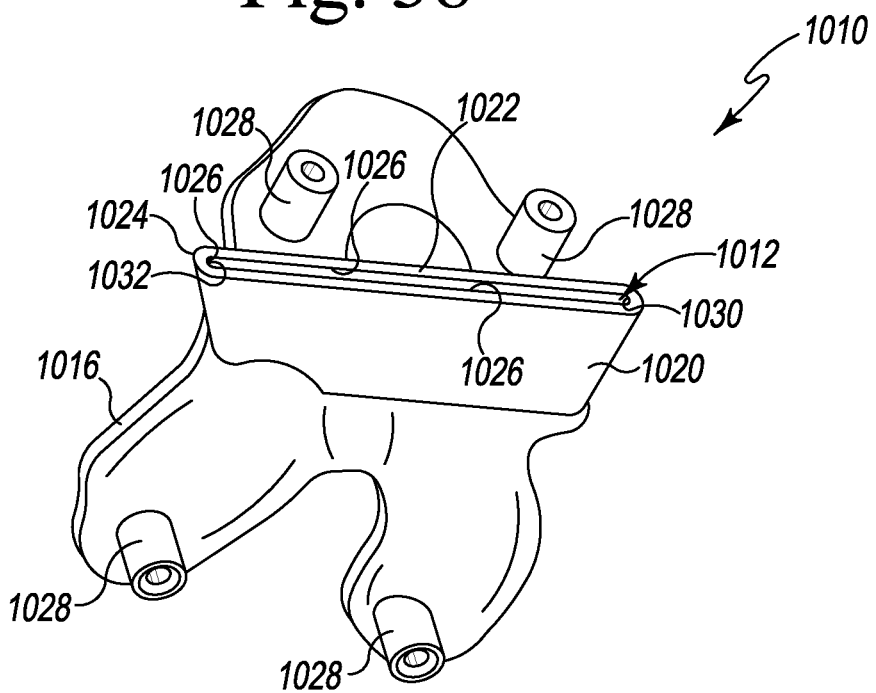
FIG. 39 of another embodiment of a customized patient-specific femoral cutting block.

Referring now to FIG. 39, the cutting block 1010 includes a cutting guide slot 1012 positioned to guide a customized, patient-specific resection of a distal end of a patient's femur. In the illustrative embodiment, the cutting block 1010 includes a number of bone-facing surfaces 1016 that have negative contours 38 that are configured to receive portions of the patient's bone.

Similar to the cutting block 710, the cutting block 1010 includes a distal resection guide body 1020 includes an elongated opening 1022 that is defined in its free end 1024 and a number of inner walls 1026 that extend inwardly from the opening 1022 to define the cutting guide slot 1012, which is sized and shaped to guide a surgical tool such as, for example, a cutting blade, into engagement with the patient's bone.

As shown in FIG. 39, the inner walls 1026 include a medial inner wall 1030 that defines the medial side of the guide slot 1012 and a lateral inner wall 1032 that defines the lateral side of the guide slot 1012. In the illustrative embodiment, the lateral inner wall 1032 extends at an oblique angle relative to the medial inner wall 1030 to guide the resection of the patient's bone. The oblique angle, like the rest of the cutting guide block 1010, is customized to the bony anatomy of the patient.

The cutting block 1010 includes a number of other surgical tool guide bodies 1028. In the illustrative embodiment, each of the tool guide bodies 1028 is a drill guide and fixation guide configured to guide a fixation pin into engagement with a patient's bone to couple the cutting block 1010 to the bone.

Figure 40:
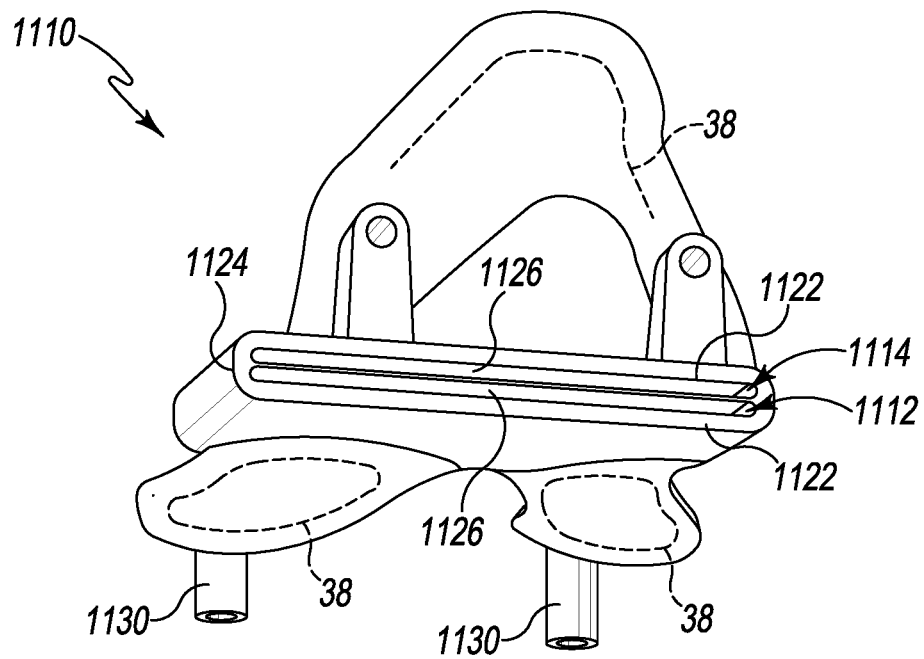
FIGS. 40-41 are perspective views of another embodiment of a customized patient-specific femoral cutting block.
Figure 41:
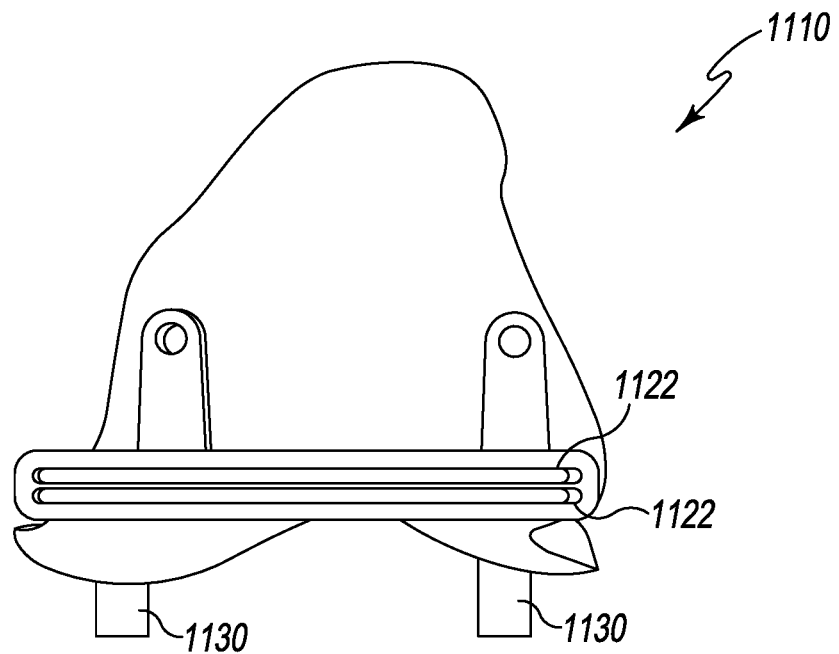

Referring now to FIGS. 40-41, the cutting block 1110 includes a pair of cutting guide slots 1112, 1114 positioned to guide a customized, patient-specific resection of a distal end of a patient's femur. In the illustrative embodiment, the cutting block 1110 includes a number of bone-facing surfaces 1116 that have negative contours 38 that are configured to receive portions of the patient's bone.

The cutting block 1110 includes a distal resection guide body 1120 includes a pair of elongated openings 1122 that are defined in its free end 1124 and a number of inner walls 1126 that extend inwardly from the openings 1122. Each opening 1122 and the inner walls 1126 cooperate to define the cutting guide slots 1112, 1114, which are sized and shaped to guide a surgical tool such as, for example, a cutting blade, into engagement with the patient's bone. The cutting guide slot 1114 is arranged distally of the cutting guide slot 1112 to offer the surgeon the option of making a second, pre-planned resection during surgery, thereby providing the surgeon with additional flexibility during surgery while at the same time maintaining the benefits of the pre-operative planning.

As shown in FIGS. 40-41, the cutting block 1110 includes a number of other surgical tool guide bodies 1130. In the illustrative embodiment, each of the tool guide bodies 1130 is a drill guide and fixation guide configured to guide a fixation pin into engagement with a patient's bone to couple the cutting block 1110 to the bone.

It should be appreciated that in some embodiments an orthopaedic surgical instrument comprising a customized patient-specific surgical instrument is disclosed. The customized patient-specific surgical instrument comprises a metallic base plate sized to be positioned on a patient's bone. The base plate has a bone-facing surface including a customized patient-specific negative contour configured to receive a corresponding positive contour of the patient's bone and an outer surface positioned opposite the bone-facing surface. The customized patient-specific surgical instrument also comprises a metallic guide body attached to, and extending from, the outer surface to a free end. The guide body includes an elongated opening that is defined in its free end. A guide slot extends from the opening in the guide body through a first opening defined in the bone-facing surface. The guide slot is sized and shaped to guide a surgical tool into engagement with the patient's bone.

In some embodiments, the guide slot may be sized and shaped to guide a fixation pin into engagement with the patient's bone. In some embodiments, the guide slot may be sized and shaped to guide a cutting saw blade into engagement with the patient's bone.

In some embodiments, the customized patient-specific surgical instrument may also comprise a boss attached to, and extending from, the outer surface to a free end spaced apart from the free end of the guide body. The boss may include an opening that is defined in its free end, and a drill guide slot may extend from the opening in the boss through a second opening defined in the bone-facing surface. The drill guide slot may be sized and shaped to guide a surgical drill or fixation pin into engagement with the patient's bone.

In some embodiments, the boss may extend from a base attached to the outer surface of the base plate to the free end.

The base may be wider than the free end, and the boss may include a tapered surface that extends from the base to the free end.

In some embodiments, the cutting guide slot may extend in an anterior-posterior direction, the drill guide slot may be a first drill guide slot extending in a superior-inferior direction, and the customized patient-specific surgical instrument may further comprise a second drill guide slot extending in an anterior-posterior direction from a second opening in the body through a third opening defined in the bone-facing surface. The second drill guide slot may be sized and shaped to guide a surgical drill into engagement with the patient's bone.

In some embodiments, the base plate may include a pair of posteriorly-extending arms. Each arm may include a portion of the customized patient-specific negative contour configured to receive a portion of the corresponding positive contour of the patient's bone.

In some embodiments, the customized patient-specific surgical instrument may include a customized patient-specific cavity that is defined in the base plate. The cavity may be sized and shaped to be positioned over a portion of the patient's bone to prevent contact between the portion of patient's bone and the customized patient-specific surgical instrument. Additionally, in some embodiments, the cavity is positioned proximal of the guide body.

In some embodiments, the base plate may include a first section attached to one of a distal end and a proximal end of the guide body, and a second section that is spaced apart from the first section of the base plate and is attached to the other of the distal end and the proximal end of the guide body.

In some embodiments, the first section may include a pair of posteriorly-extending arms. Each arm may include a portion of the customized patient-specific negative contour configured to receive a portion of the corresponding positive contour of the patient's bone. Additionally, in some embodiments, the customized patient-specific surgical instrument may include a plurality of openings extending through the bone-facing and outer surfaces of the posterior-extending arms of the first section and the bone-facing and outer surfaces of the second section of the base plate.

In some embodiments, the customized patient-specific surgical instrument may be a single monolithic metallic component including a plurality of laminations.

It should be appreciated that in some embodiments a customized patient-specific surgical instrument comprises a metallic guide body extending from a posterior end to a free anterior end. The guide body includes an elongated opening that is defined in its free anterior end. A cutting guide slot extends from the opening in the guide body. The guide slot is sized and shaped to guide a cutting saw blade into engagement with a patient's bone. The customized patient-specific surgical instrument also includes a first plate section extending from the posterior end of the metallic guide body, and the first plate section includes a pair of posterior-extending arms. Each arm includes a first portion of a customized patient-specific negative contour configured to receive a first portion of a corresponding positive contour of the patient's bone. The customized patient-specific surgical instrument also includes a second plate section spaced apart from the first plate section and extending from the posterior end of the metallic guide body. The second plate section includes a bone-facing surface including a second portion of the customized patient-specific negative contour configured to receive a second portion of the corresponding positive contour of the patient's bone.

In some embodiments, the customized patient-specific surgical instrument may also comprise a first boss attached to, and extending from, the second plate section to an end spaced apart from the free anterior end of the guide body. The first boss may include an opening that is defined in its end, and a first drill guide slot may extend from the opening in the first boss. The first drill guide slot may be sized and shaped to guide a surgical drill into engagement with the patient's bone.

In some embodiments, the customized patient-specific surgical instrument may further comprise a second boss attached to, and extending from a first arm of the pair of posterior-extending arms to a free end. the second boss may include an opening that is defined in its free end, and a second drill guide slot extending from the opening in the second boss. The second drill guide slot may be sized and shaped to guide a surgical drill into engagement with the patient's bone.

In some embodiments, the customized patient-specific surgical instrument may further comprise a third boss attached to, and extending from, a second arm of the pair of posterior-extending arms to a free end. The third boss may include an opening that is defined in its free end, and a third drill guide slot extending from the opening in the third boss. The third drill guide slot may be sized and shaped to guide a surgical drill into engagement with the patient's bone.

Additionally, in some embodiments, the customized patient-specific surgical instrument may be a single monolithic metallic component including a plurality of laminations.

It should be appreciated that in some embodiments a single monolithic metallic customized patient-specific surgical instrument includes a plurality of laminations of metallic material. The single monolithic metallic customized patient-specific surgical instrument includes a bone-facing surface configured to engage a patient's bone. The bone-facing surface includes a customized patient-specific negative contour configured to receive a corresponding positive contour of the patient's bone. The single monolithic metallic customized patient-specific surgical instrument includes an outer surface positioned opposite the bone-facing surface, and a guide slot defined in the bone-facing surface. The guide slot is sized and shaped to guide a surgical tool into engagement with the patient's bone.

It should be appreciated that in some embodiments a method of manufacturing a customized patient-specific orthopaedic surgical instrument comprises generating a three-dimensional model of a patient's bone based on patient-specific data, identifying a first region of the three-dimensional model of the patient's bone, defining an outer boundary of a customized patient-specific surgical instrument on the three-dimensional model of the patient's bone, generating a customized patient-specific surgical instrument model within the outer boundary, the customized patient-specific surgical instrument model comprising a bone-facing surface including a customized patient-specific negative contour that receives a corresponding positive contour of the patient's bone, and fabricating the customized patient-specific orthopaedic surgical instrument from metallic material based on the customized patient-specific surgical instrument model. The step of generating the customized patient-specific surgical instrument model comprises defining a cavity in the bone-facing surface over the first region of the three-dimensional model of the patient's bone. The cavity has an outer edge that is aligned with or larger than the outer edge of the first region. The step of generating the customized patient-specific surgical instrument model also comprises generating an outer surface of the customized patient-specific surgical instrument opposite the bone-facing surface, extending a guide body outward from the outer surface of the customized patient-specific surgical instrument model to a free end, and defining a guide slot in the guide body, the guide slot being sized and shaped to guide a surgical tool into engagement with the patient's bone.

In some embodiments, method may also comprise identifying a planned resection plane on the three-dimensional model of the patient's bone based on the patient-specific data. The step of defining the guide slot through the guide body may include aligning the guide slot with the planned resection plane, and sizing and shaping the guide slot to guide the cutting saw blade along the planned resection plane into engagement with the patient's bone.

Additionally, in some embodiments, the step of sizing and shaping the guide slot includes defining the guide slot between a medial sidewall and a lateral sidewall of the guide body, and at least one of the medial sidewall and the lateral sidewall are angled relative to the other of the medial sidewall and the lateral sidewall.

In some embodiments, the guide slot may be a first guide slot, and generating the customized patient-specific surgical instrument model may further comprise extending a boss outward from the outer surface of the customized patient-specific surgical instrument model to a free end that is spaced apart from the free end of the guide body and defining a drill guide slot in the boss. In some embodiments, the step of extending the boss outward from the outer surface may include defining a tapered surface on a first side of the boss, and fabricating the customized patient-specific orthopaedic surgical instrument from metallic material includes layering metallic material in a fabrication machine such that the tapered surface faces downward in the fabrication machine.

In some embodiments, the step of generating the customized patient-specific surgical instrument model may further comprise defining a plurality of apertures that extend through the outer surface and the bone-facing surface.

In some embodiments, the step of generating the customized patient-specific surgical instrument model may further comprise defining a second plurality of apertures through the guide body of the customized patient-specific surgical instrument model. Additionally, in some embodiments, each of the apertures may include a diamond-shaped opening.

In some embodiments, the step of extending the guide body outward from the outer surface of the customized patient-specific surgical instrument model to the free end may include defining a tapered surface on a first side of the guide body, and fabricating the customized patient-specific orthopaedic surgical instrument from metallic material may include layering metallic material in a fabrication machine such that the tapered surface faces downward in the fabrication machine.

In some embodiments, the step of fabricating the customized patient-specific orthopaedic surgical instrument from metallic material based on the customized patient-specific surgical instrument model may include forming the customized patient-specific orthopaedic surgical instrument as a single monolithic component.

In some embodiments, the single monolithic component may include a plurality of laminations of metallic material.

It should be appreciated that in some embodiments the method of manufacturing a customized patient-specific orthopaedic surgical instrument comprises generating a three-dimensional model of a patient's bone based on patient-specific data, defining an outer boundary of a customized patient-specific surgical instrument on the three-dimensional model of the patient's bone, generating a customized patient-specific surgical instrument model within the outer boundary, the customized patient-specific surgical instrument model including a customized patient-specific bone facing surface, and fabricating the customized patient-specific orthopaedic surgical instrument from metallic material based on the customized patient-specific surgical instrument model. The step of generating the customized patient-specific surgical instrument model comprises generating an outer surface of the customized patient-specific surgical instrument opposite the bone-facing surface, extending a guide body outward from the outer surface of the customized patient-specific surgical instrument model to a free end, and defining a guide slot in the guide body. The guide slot may be sized and shaped to guide a surgical tool into engagement with the patient's bone.

In some embodiments, the method may include planning a resected surface of the patient's bone, and generating the customized patient-specific surgical instrument model may include shaping an outer edge of the bone-facing surface to match an outer edge of the planned resected surface of the patient's bone.

In some embodiments, the guide body may be a first guide body, and generating the customized patient-specific surgical instrument model further may comprise extending a second guide body outward from the outer surface of the customized patient-specific surgical instrument model to an end spaced apart from the free end of the first guide body, defining a second guide slot in the second guide body, the second guide slot being sized and shaped to guide a surgical tool into engagement with the patient's bone and extending transverse to the first guide slot.

In some embodiments, the step of generating the customized patient-specific surgical instrument model may further comprise extending a third guide body outward from the outer surface of the customized patient-specific surgical instrument model to a free end spaced apart from the first guide body, and defining a third guide slot the second guide slot being sized and shaped to guide a surgical tool into engagement with the patient's bone and intersecting the second cutting guide slot.

Additionally, in some embodiments, the second guide body may include a boss having a tapered outer surface, and the second guide slot may be a drill guide slot sized and shaped to guide a surgical drill into engagement with the patient's bone.

In some embodiments, the step of fabricating the customized patient-specific orthopaedic surgical instrument from metallic material based on the customized patient-specific surgical instrument model may include forming the customized patient-specific orthopaedic surgical instrument as a single monolithic component.

In some embodiments, the step of fabricating the customized patient-specific orthopaedic surgical instrument may include operating a three-dimensional metal printer to fabricate the customized patient-specific surgical instrument by forming laminations of metallic material.

It should be appreciated that in some embodiments the method of designing a customized patient-specific orthopaedic surgical instrument comprises generating a three-dimensional model of a patient's bone based on patient-specific data, defining an outer boundary of a customized patient-specific surgical instrument on the three-dimensional model of the patient's bone, and generating a customized patient-specific surgical instrument model within the outer boundary. The customized patient-specific surgical instrument model includes a customized patient-specific bone facing surface. In some embodiments, generating the customized patient-specific surgical instrument model comprises generating an outer surface of the customized patient-specific surgical instrument opposite the bone-facing surface, extending a guide body outward from the outer surface of the customized patient-specific surgical instrument model to a free end, and defining a guide slot in the guide body, the guide slot being sized and shaped to guide a surgical tool into engagement with the patient's bone.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An orthopaedic surgical system comprising:
a first customized patient-specific surgical instrument, comprising:
a first base plate sized to be positioned on a patient's femur, the base plate having (i) a first bone-facing surface including a customized patient-specific negative contour configured to receive a corresponding positive contour of the patient's femur and (ii) a first outer surface positioned opposite the first bone-facing surface, and
a first guide body attached to, and extending from, the first outer surface to a first free distal end, the first guide body including a first cutting guide slot sized to receive a cutting saw blade to form a resected surface on the patient's femur, and
a second customized patient-specific surgical instrument, comprising:
a second base plate sized to be positioned on the resected surface of the patient's femur, the second base plate having (i) a second bone-facing surface configured to contact the resected surface of the patient's femur, (ii) a second outer surface positioned opposite the second bone-facing surface, and (iii) a customized patient-specific outer edge extending between the second bone-facing surface and the second outer surface, wherein the customized patient-specific outer edge is shaped to match an outer edge of the resected surface of the patient's femur, and
a second guide body attached to, and extending from, the second outer surface to a second free distal end, the second guide body including a second cutting guide slot sized to receive the cutting saw blade.

2. The orthopaedic surgical system of claim 1, wherein the first cutting guide slot is configured to receive the cutting saw blade to resect a distal end of the patient's femur to form the resected surface.

3. The orthopaedic surgical system of claim 1, wherein the outer edge of the second base plate includes a superior section that is curved to match a curvature of an anterior edge section of the outer edge of the resected surface.

4. The orthopaedic surgical system of claim 1, wherein the outer edge of the second base plate includes an inferior section that is curved to match a curvature of a posterior edge section of the outer edge of the resected surface.

5. The orthopaedic surgical system of claim 1, wherein the second base plate includes a superior notch that is shaped to match a distal opening of a trochlear groove of the patient's femur.

6. The orthopaedic surgical system of claim 1, wherein the second base plate includes an inferior notch that is shaped to match a distal opening of an intercondylar notch of the patient's femur.

7. The orthopaedic surgical system of claim 1, wherein the second customized patient-specific surgical instrument further comprises a third guide body attached to, and extending from, the second outer surface to a third free distal end, the third guide body including a third cutting guide slot sized to receive the cutting saw blade.

8. The orthopaedic surgical system of claim 7, wherein the third cutting guide slot extends obliquely relative to the second cutting guide slot.

9. A customized patient-specific surgical instrument, comprising:
a base plate sized to be positioned on a resected surface of a patient's femur, the base plate having (i) a bone-facing surface configured to contact the resected surface of the patient's femur, (ii) an outer surface positioned opposite the bone-facing surface, and (iii) a customized patient-specific outer edge extending between the bone-facing surface and the outer surface, wherein the customized patient-specific outer edge is shaped to match an outer edge of the resected surface of the patient's femur, and
a guide body attached to, and extending from, the outer surface to a free distal end, the guide body including a cutting guide slot sized to receive a cutting saw blade.

10. The customized patient-specific surgical instrument of claim 9, wherein the resected surface is a resected distal end of the patient's femur.

11. The customized patient-specific surgical instrument of claim 9, wherein the outer edge of the base plate includes a superior section that is curved to match a curvature of an anterior edge section of the outer edge of the resected surface.

12. The customized patient-specific surgical instrument of claim 9, wherein the outer edge of the base plate includes an inferior section that is curved to match a curvature of a posterior edge section of the outer edge of the resected surface.

13. The customized patient-specific surgical instrument of claim 9, wherein the base plate includes a superior notch that is shaped to match a distal opening of a trochlear groove of the patient's femur.

14. The customized patient-specific surgical instrument of claim 9, wherein the base plate includes an inferior notch that is shaped to match a distal opening of an intercondylar notch of the patient's femur.

15. The customized patient-specific surgical instrument of claim 9, wherein the guide body is a first guide body that includes a first cutting guide slot, and wherein the customized patient-specific surgical instrument further comprises a second guide body attached to, and extending from, the outer surface to a second free distal end, the second guide body including a second cutting guide slot sized to receive the cutting saw blade.

16. The customized patient-specific surgical instrument of claim 15, wherein the second cutting guide slot extends obliquely relative to the first cutting guide slot.

17. A method of resecting a patient's femur, comprising:
resecting a patient's bone to form a first resected surface on the patient's bone,
positioning a customized patient-specific surgical instrument in contact with the first resected surface of the patient's bone, and
aligning an outer perimeter edge of the first resected surface with a customized, patient-specific outer edge of a bone-facing surface of the customized patient-specific surgical instrument.

18. The method of claim 17, further comprising inserting a cutting saw through a cutting guide slot defined in the customized patient-specific surgical instrument to form a second resected surface on the patient's bone.

19. The method of claim 17, wherein resecting the patient's bone to form the first resected surface on the patient's bone comprises resecting a distal end of the patient's femur.

20. The method of claim 19, wherein aligning the outer perimeter edge of the first resected surface with the customized, patient-specific outer edge of the bone-facing surface of the customized patient-specific surgical instrument comprises at least one of:
aligning a curved superior section of the customized, patient-specific outer edge to a curvature of an anterior edge section of the outer perimeter edge of the first resected surface,
aligning a curved inferior section of the customized, patient-specific outer edge to a curvature of a posterior edge section of the outer perimeter edge of the first resected surface,
aligning a superior notch in the customized, patient-specific outer edge to a distal opening of a trochlear groove of the patient's femur, and
aligning an inferior notch in the customized, patient-specific outer edge to a distal opening of an intercondylar notch of the patient's femur.

\* \* \* \* \*